(12) United States Patent
Brodie et al.

(10) Patent No.: US 7,875,599 B2
(45) Date of Patent: Jan. 25, 2011

(54) C-17-HETEROARYL STEROIDAL CYP17 INHIBITORS/ANTIANDROGENS, IN VITRO BIOLOGICAL ACTIVITIES, PHARMACOKINETICS AND ANTITUMOR ACTIVITY

(75) Inventors: Angela Brodie, Fulton, MD (US); Vincent Njar, Glen Burnie, MD (US)

(73) Assignee: University of Maryland, Baltimore, MD (US)

( * ) Notice: Subject to any disclaimer, the term of this patent is extended or adjusted under 35 U.S.C. 154(b) by 398 days.

(21) Appl. No.: 11/817,550

(22) PCT Filed: Mar. 2, 2006

(86) PCT No.: PCT/US2006/007143

§ 371 (c)(1),
(2), (4) Date: Mar. 14, 2008

(87) PCT Pub. No.: WO2006/093993

PCT Pub. Date: Sep. 8, 2006

(65) Prior Publication Data

US 2008/0280864 A1 Nov. 13, 2008

Related U.S. Application Data

(60) Provisional application No. 60/657,390, filed on Mar. 2, 2005.

(51) Int. Cl.
*A61K 31/58* (2006.01)
(52) U.S. Cl. .................................................... 514/176
(58) Field of Classification Search .................. 514/176
See application file for complete search history.

(56) References Cited

U.S. PATENT DOCUMENTS

| 5,604,213 | A | 2/1997 | Barrie et al. |
| 5,994,335 | A | 11/1999 | Brodie et al. |
| 6,200,965 | B1 | 3/2001 | Brodie et al. |
| 6,444,683 | B2 | 9/2002 | Brodie et al. |

FOREIGN PATENT DOCUMENTS

| WO | WO-2005-014023 A1 | 2/2005 |
| WO | WO-2006-093993 A1 | 9/2006 |

OTHER PUBLICATIONS

Vasaitis, T. et al., "Androgen Receptor Inactivation Contributes to Antitumor Efficacy of CYP17 Inhibitor VN/124-1 in Prostate Cancer," Mol. Cancer Therapeutics 7(8):2348-2357 (2008).
Vasaitis, T. et al., "The Effects of Novel Anti-Androgens on Androgen Receptor Action and Expression," Proceedings of the American Association for Cancer Research 47, Abstract 5340 (2006) http://aacrmeetingabstracts.org/cgi/content/abstract/2006/1/252-d.
PCT/US09/36891 Search Report dated Oct. 7, 2009.

Kadar et al., "Technical and safety aspects of blood and marrow transplantation using G-CSF mobilized family donors," Transfusion Science 17(4):611-618 (1996).
Clement, et al., "Three Dimensional Pharmacophore Modeling of Human CYP17 Inhibitors Potential Agents for Prostate Cancer Therapy" J. Med. Chem. 46 (2003): 2345-2351.
Handratta et al., "Novel C-17-heteroaryl steroidal CYP17 inhibitors/antiandrogens: synthesis, in vitro biological activity, pharmacokinetics, and antitumor activity in the LAPC4 human prostate cancer xenograft model", J. Med. Chem., 48(8), pp. 2972-2984 (2005).
Potter et al., "A convenient large-scale synthesis of abiraterone acetate 3beta -acetoxy-17-(3-pyridyl)androsta-5,16-diene, a potential new drug for the treatment of prostate cancer", Organic Preparations and Procedures International, 29(1), pp. 123-128 (1997).
Supplementary European Search Report for European Application No. EP 06736460, Jul. 29, 2009.
Bruchovsky and Wilson, "The conversion of testosterone to 5-alpha-androstan-17-beta-ol-3-one by rat prostate in vivo and in vitro," J Biol Chem 243(8):2012-21, 1968.
Chen et al., "Molecular determinants of resistance to antiandrogen therapy," Nat Med 10(1):33-9, 2004.
Chengjie et al., "Synthesis of pharmacological activity of some 17-[(2 '-substituted)-4'-pyramidyl]androstene derivatives as inhibitors of human 17α-hydroxylase/$C_{17,20}$-layse," J Chinese Pharm Sci 10(1):3-8, 2001.
Choshi et al., "Total synthesis of grossularines-1 and -2," J Org Chem 60:5899-5904, 1995.
Crawford et al., "Treatment of newly diagnosed stage D2 prostate cancer with leuprolide and flutamide or leuprolide alone, phase III: prognostic significance of minimal disease," J Urol 147:417A, 1992.
Crawford et al., "A controlled trial of leuprolide with and without flutamide in prostatic carcinoma," New Eng J Med 321:419-424, 1989.
Denis, "Role of maximal androgen blockade in advanced prostate cancer," The Prostate Supplement 5:17-22, 1994.
Denmeade and Isaacs, "A history of prostate cancer treatment," Nat Rev Cancer 2(5):389-96, 2002.
Evans et al., "Methods for drug discovery: development of potent, selective, orally effective cholecystokinin antagonists," J Med Chem 31(12):2235-46, 1988.
Grigoryev et al., "Cytochrome P450c17-expressing *Escherichia coli* as a first-step screening system for 17alpha-hydroxylase-C17,20-lyase inhibitors," Anal Biochem 267(2):319-30, 1999.

(Continued)

*Primary Examiner*—Barbara P Badio
(74) *Attorney, Agent, or Firm*—Wilson Sonsini Goodrich & Rosati

(57) ABSTRACT

Described are steroidal C-17 benzoazoles, pyrimidinoazoles (azabenzoazoles) and diazines. Methods for their synthesis are also described, which include methods having a step of nucleophilic vinylic "addition-elimination" substitution reaction of 3β-acetoxy-17-chloro-16-formylandrosta-5,16-diene or analogs thereof and benzoazole or pyrimidinoazole nucleophiles and methods having a palladium catalyzed cross-coupling reaction of 17-iodoandrosta-5,16-dien-3β-ol or analogs thereof with tributylstannyl diazines. The compounds are potent inhibitors of human CYP 17 enzyme as well as potent antagonists of both wild type and mutant androgen receptors (AR). The compounds are useful for the treatment of human prostate cancer.

17 Claims, 8 Drawing Sheets

OTHER PUBLICATIONS

Figure 1:
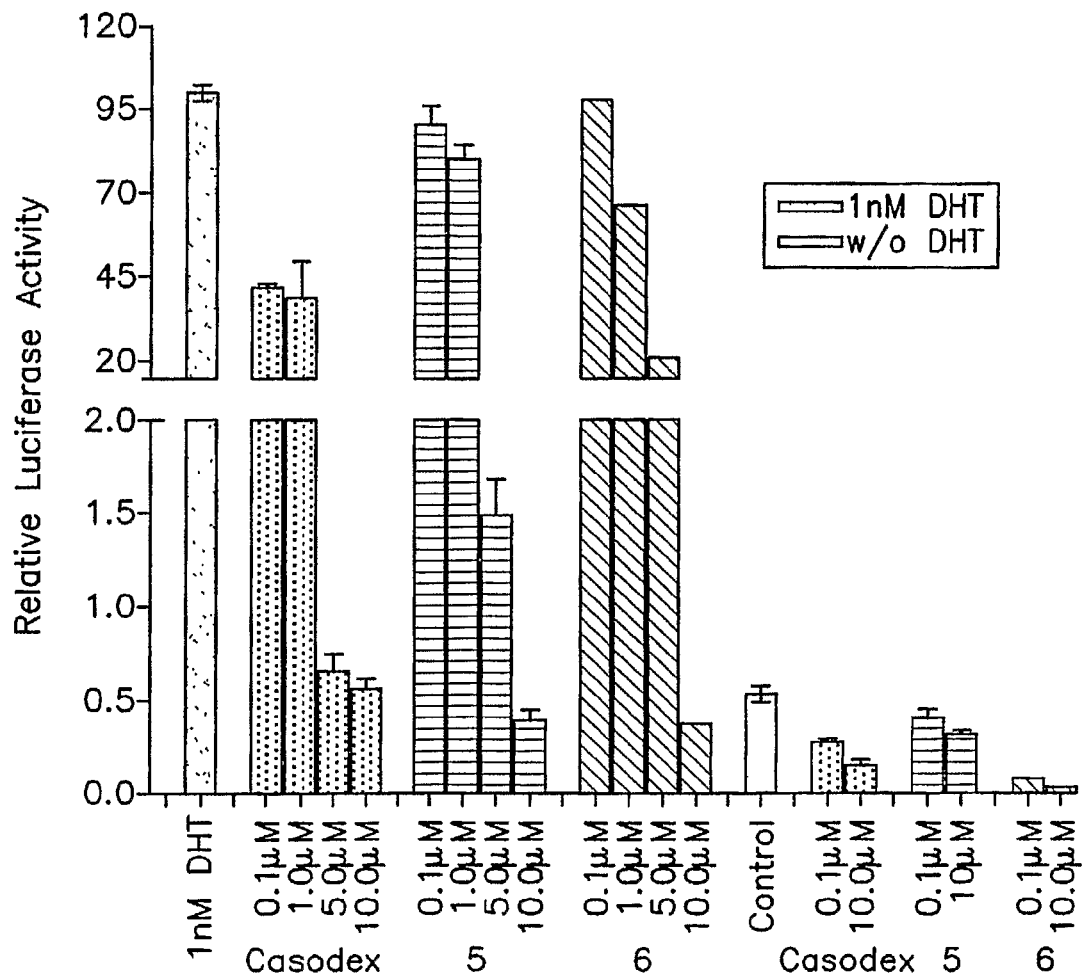

Grigoryev et al., "Effects of new 17α-hydroxylase/C(17,20)-lyase inhibitors on LNCaP prostate cancer cell growth in vitro and in vivo," Br J Cancer 81(4):622-30, 1999.

Haidar et al., "Novel steroidal pyrimidyl inhibitors of P450 17 (17 alpha-hydroxylase/C17-20-lyase)," Arch Pharm (Weinheim) 334(12):373-4, 2001.

Hall, "Cytochrome P-450 C21scc: one enzyme with two actions: hydroxylase and lyase," J Steroid Biochem Mol Biol 40(4-6):527-32, 1991.

Huggins et al., "Studies of prostatic cancer: II. the effects of castration on advanced carcinoma of the prostate gland," *Arch Surg* 43(2):209-223, 1941.

Jefcoate, "Measurement of substrate and inhibitor binding to microsomal cytochrome P-450 by optical-difference spectroscopy," Methods Enzymol 52:258-79, 1978.

Jemal et al., "Cancer statistics, 2004," CA Cancer J Clin 54(1):8-29, 2004.

Kim et al., "Synergism of cytoplasmic kinases in IL6-induced ligand-independent activation of androgen receptor in prostate cancer cells," Oncogene 23(10):1838-44, 2004.

Klein et al., "Progression of metastatic human prostate cancer to androgen independence in immunodeficient SCID mice," Nat Med (4):402-8, 1997.

McConnell, "Physiologic basis of endocrine therapy for prostatic cancer," Urol Clin North Am 18(1):1-13, 1991.

Mohler et al., "The androgen axis in recurrent prostate cancer," Clin Cancer Res 10(2):440-8, 2004.

Muscato et al., "Optimal dosing of ketoconazole (Keto) and hydrocortisone (HC) leads to long responses in hormone refractory prostate cancer," Proc ASCO 229:701, 1994.

Nicolaou et al., "Natural product-like combinatorial libraries based on privileged structures. 1. General principles and solid-phase synthesis of benzopyrans," J Am Chem Soc 122:9939-9953, 2000.

Njar and Brodie, "Inhibitors of 17alpha-hydroxylase/17,20-lyase (CYP17): potential agents for the treatment of prostate cancer," Curr Pharm Des 5(3):163-80, 1999.

O'Donnell et al., "Hormonal impact of the 17alpha-hydroxylase/C(17,20)-lyase inhibitor abiraterone acetate (CB7630) in patients with prostate cancer," Br J Cancer 14;90(12):2317-25, 2004.

Picard et al., "Synthesis and evaluation of 2'-substituted 4-(4'-carboxy- or 4'carboxymethylbenzylidene)-N-acylpiperidines: highly potent and in vivo active steroid 5alpha-reductase type 2 inhibitors," : J Med Chem 45(16):3406-17, 2002.

Potter et al., "A convenient, large-scale synthesis of abiraterone acetate [3B-acetoxy-17-(3-pryidyl)androsta-5,16-diene], a potential new drug for the treatment of prostate cancer," Organic Preparations and Procedures Int.29(1):123-134 (1997).

Small et al., "Ketoconazole retains activity in advanced prostate cancer patients with progression despite flutamide withdrawal," J Urol 157(4):1204-7, 1997.

Thompson and Wilding, "Androgen antagonist activity by the antioxidant moiety of vitamin E, 2,2,5,7,8-pentamethyl-6-chromanol in human prostate carcinoma cells," Mol Cancer Ther 2(8):797-803, 2003.

Tindall et al., "Symposium on androgen action in prostate cancer," Cancer Res 64(19):7178-80, 2004.

Trachtenberg et al., "Ketoconazole: a novel and rapid treatment for advanced prostatic cancer," J Urol 130(1):152-3, 1983.

Zhang et al., "A small composite probasin promoter confers high levels of prostate-specific gene expression through regulation by androgens and glucocorticoids in vitro and in vivo," Endocrinology 141(12):4698-710, 2000.

Ru et al., Synthesis and Pharmacological Activity fo Some 17-[2'-substituted)-4'-pyrimidyl] androstene derivativies as inhibitors of human 17alpha-hydroxylase/C17,20-lyse., J. Chin. Pharm. Sci., Jun. 2001, vol. 10, No. 1, pp. 3-8.

Barrie et al., "Pharmacology of novel steroidal inhibitors of cytochrome $P450_{17\alpha}$ (17α-hydroxylase/C17-20 lyase)", J. Steroid Biochem. Mol. Biol., 50(5-6):267-273 (1994).

Haidar et al., "Effects of novel 17α-hydroxylase/C17, 20-lyase (P450 17, CYP 17) inhibitors on androgen biosynthesis in vitro and in vivo", J. Steroid Biochem. Mol. Biol., 84: 555-562 (2003).

Handratta et al., "Potent CYP17 inhibitors: improved syntheses, pharmacokinetics and anti-tumor activity in the LNCaP human prostate cancer model", J. Steroid Biochem. Mol. Biol., 92: 155-165 (2004).

Jarman et al., "The 16,17-Double Bond Is Needed for Irreversible Inhibition of Human Cytochrome P450 by Abiraterone (17-(3-Pyridyl)androsta-5,16-dien-3β-ol) and Related Steroidal Inhibitors", J. Med. Chem., 41 (27): 5375-5381 (1998).

Ling et al., "17-Imidazolyl, Pyrazolyl, and Isoxazolyl Androstene Derivatives. Novel Steroidal Inhibitors of Human Cytochrome $C_{17,20}$-Lyase (P450$_{17\alpha}$)", J. Med. Chem., 40 (20): 3297-3304 (1997).

Long et al., "Antiandrogenic Effects of Novel Androgen Synthesis Inhibitors on Hormone-dependent Prostate Cancer", Cancer Research, 60: 6630-6640 (2000).

Matsunaga et al., "Synthetic studies on (1S)-1-(6,7-dimethoxy-2-naphthyl)-1-(1H-imidazol-4-yl)-2-methylpropan-1-ol as a selective $C_{17,20}$-lyase inhibitor", Tetrahedron: Asymmetry, 15: 2021-2028 (2004).

Matsunaga et al., "$C_{17,20}$-Lyase inhibitors I. Structure-based de novo design and SAR study of $C_{17,20}$-lyase inhibitors", Bioorganic & Medicinal Chemistry, 12: 2251-2273 (2004).

Matsunaga et al., "$C_{17,20}$-lyase inhibitors. Part 2: Design, synthesis and structure—activity relationships of (2-naphthylmethyl)-1H-imidazoles as novel $C_{17,20}$-lyase inhibitors", Bioorganic & Medicinal Chemistry, 12: 4313-4336 (2004).

Njar et al., "Nucleophilic vinylic "addition-elimination" substitution reaction of 3β-acetoxy-17-chloro-16-formylandrosta-5,16-diene: A novel and general route to 17-substituted steroids. Part 1—synthesis of novel 17-azolyl-$\Delta^{16}$ steroids; inhibitors of 17α-hydroxylase/17,20-lyase (17α-lyase)", Bioorganic & Medicinal Chemistry Letters, 6(22): 2777-2782 (1996).

Njar et al., "Novel 17-Azolyl Steroids, Potent Inhibitors of Human Cytochrome 17α-Hydroxylase-$C_{17,20}$-lyase (P450$_{17\alpha}$): Potential Agents for the Treatment of Prostate Cancer", J. Med. Chem., 41(6): 902-912 (1998).

Nnane et al., "Effects of novel 17-azolyl compounds on androgen synthesis in vitro and in vivo", J. Steroid Biochem. Mol. Biol., 71: 145-152 (1999).

Ojida et al., "Stereocontrolled synthesis of (1S)-1-(1H-imidazol-4-yl)-1-(6-methoxy-2-naphthyl)-2-methylpropan-1-ol as a potent $C_{17,20}$-lyase inhibitor", Tetrahedron: Asymmetry, 15: 1555-1559 (2004).

Potter et al., "Novel Steroidal Inhibitors of Human Cytochrome P450$_{17\alpha}$(17α-Hydroxylase-$C_{17,20}$-lyase): Potential Agents for the Treatment of Prostatic Cancer", J. Med. Chem., 38(13): 2463-2471 (1995).

NIH Grant Project Reference No. 5RO1CA27440-27 ESNAP Report, approximate submission date May 8, 2006.

NIH Grant Project Reference No. 5RO1 CA27440-27 Grant Continuation Application and Progress Report, approximate submission date Apr. 26, 2006.

NIH Grant Project Reference No. 5RO1 CA27440-26 Grant Continuation Application and Progress Report, approXimate submission date Jul. 1, 2005; approximate award date Aug. 2, 2005.

NIH Grant Project Reference No. 2RO1 CA27440-24A1, 2R01 CA27440-25A1 Revised Grant Renewal Application, approximate submission date Feb. 18, 2004; approximate award date Sep. 23, 2004.

NIH Grant Project Reference No. 5RO1 CA27440-25 Grant Renewal Application, approximate submission date Jun. 26, 2003—Unfunded.

NIH Grant Project Reference No. 5RO1 CA27440-24 Grant Continuation Application and Progress Report, approximate date Feb. 20, 2003; approximate award date Jun. 3, 2003.

NIH Grant Project Reference No. 3RO1 CA27440-23S1 Grant Continuation Application and Progress Report, approximate date May 3, 2002; approximate award date Jun. 21, 2002.

NIH Grant Project Reference No. 5RO1 CA27440-23 Grant Continuation Application and Progress Report, approximate date Jan. 21, 2002; approximate award date Apr. 29, 2002.

Abstract of NIH Grant Project Reference No. 5RO1 CA27440-27, approximate submission date Apr. 26, 2006.

Abstract of NIH Grant Project Reference No. 5RO1 CA27440-26, approximate submission date Jul. 1, 2005; approximate award date Aug. 2, 2005.

Abstract of NIH Grant Project Reference No. 2R01 CA27440-25A1, approximate submission date Feb. 18, 2004; approximate award date Sep. 23, 2004.

Abstract of NIH Grant Project Reference No. 5RO1 CA27440-24S1, approximate date Apr. 1, 2003; approximate award date Jun. 3, 2003.

Abstract ANIH Grant Project Reference No. 5RO1 CA27440-24, approximate date Feb. 20, 2003; approximate award date Jun. 3, 2003.

Abstract of NIH Grant Project Reference No. 3RO1 CA27440-23S1, approximate date May 3, 2002; approximate award date Jun. 21, 2002.

Abstract of NIH Grant Project Reference No. 5RO1 CA27440-23, approximate date Jan. 21, 2002; approximate award date Apr. 29, 2002.

Abstract of NIH Grant Project Reference No, 3RO1 CA27440-22S1, approximate date Jun. 21, 2001; approximate award date Aug. 17, 2001.

NIH Grant Project Reference No. 5R)1 CA27440-24S1 Grant Continuation Application and Progress Report, approximate date Apr. 1, 2003; approximate award date Jun. 3, 2003.

NIH Grant Project Reference No. 3R)1 CA27440-22S1 Grant Application for Supplemental Funding, approximate date Jun. 21, 2001; approximate award date Aug. 17, 2001.

C-17-HETEROARYL STEROIDAL CYP17 INHIBITORS/ANTIANDROGENS, IN VITRO BIOLOGICAL ACTIVITIES, PHARMACOKINETICS AND ANTITUMOR ACTIVITY

This application is a 371 of PCT/US06/07143 filed Mar. 2, 2006 which claims the benefit of the filing date of U.S. Provisional Application Ser. No. 60/657,390 filed Mar. 2, 2005, which is incorporated by reference herein.

This invention was made with government support under Grant No. CA27440 awarded by the National Institutes of Health (NIH). The government has certain rights in the invention.

The present invention provides new chemical entities, particularly steroidal C-17 benzoazoles, pyrimidinoazoles (azabenzoazoles) and diazines. It is also provides methods for the synthesis of the benzoazoles, pyrimidinoazoles and diazines. In one embodiment, the methods for synthesizing benzoazoles or pyrimidinoazoles comprise a step of nucleophilic vinylic "addition-elimination" substitution reaction of 3β-acetoxy-17-chloro-16-formylandrosta-5,16-diene or analogs thereof and benzoazole or pyrimidinoazole nucleophiles. In another embodiment, the methods for synthesizing diazines comprise a palladium catalyzed cross-coupling reaction of 17-iodoandrosta-5,16-dien-3β-ol or analogs thereof with tributylstannyl diazines.

Compounds of the present invention are potent inhibitors of human CYP17 enzyme as well as potent antagonists of both wild type and mutant androgen receptors (AR). The most potent CYP17 inhibitors were: 3β-hydroxy-17-(1H-benzimidazole-1-yl)androsta-5,16-diene (5, code named VN/124-1), 3β-hydroxy-17-($5^1$-pyrimidyl)androsta-5,16-diene (15) and 17-(1H-benzimidazole-1-yl)androsta-4,16-diene-3-one (6), with $IC_{50}$ values of 300, 500 and 915 nM, respectively. Compounds 5, 6, 14 and 15 were effective at preventing binding of $^3$H-R1881 (methyltrienolone, a stable synthetic androgen) to both the mutant and LNCaP AR and the wild-type AR, but with a 2.2 to 5-fold higher binding efficiency to the latter. Compounds 5 and 6 were also shown to be potent pure AR antagonists. The cell growth studies showed that 5 and 6 inhibit the growth of DHT-stimulated LNCaP and LAPC4 prostate cancer cells with $IC_{50}$ values in the low micromolar range (i.e., <10 μM). Their inhibitory potencies were comparable to that of casodex but remarkably superior to that of flutamide. The pharmacokinetics of compounds 5 and 6 in mice was investigated. Following s.c. administration of 50 mg/kg of 5 and 6, peak plasma levels of 16.82 and 5.15 ng/mL, respectively occurred after 30 to 60 min, both compounds were cleared rapidly from plasma (terminal half-lives of 44.17 and 39.93 min, respectively) and neither was detectable at 8 h. Remarkably, compound 5 was rapidly converted into a metabolite tentatively identified as 17-(1H-benzimidazol-1-yl)androsta-3-one. When tested in vivo, 5 proved to be very effective at inhibiting the growth of androgen-dependent LAPC4 human prostate tumor xenograft, while 6 was ineffective. Compound 5 (50 mg/kg/ twice daily) resulted in a 93.8% reduction (P=0.00065) in the mean final tumor volume compared with controls, and it was also significantly more effective than castration. To our knowledge, this is the first example of an anti-hormonal agent (an inhibitor of androgen synthesis (CYP17 inhibitor)/antiandrogen) that is significantly more effective than castration in suppression of androgen-dependent prostate tumor growth. In view of these impressive anti-cancer properties, compound 5 and others can be used for the treatment of human prostate cancer.

Prostate cancer (PCA) is the most common malignancy and age-related cause of cancer death worldwide. Apart from lung cancer, PCA is the most common form of cancer in men and the second leading cause of death in American men. In the United States this year (2004), an estimated 230,000 new case of prostate cancer will be diagnosed and about 23,000 men will die of this disease (Jemal et al., Cancer Statistics, 2004. *CA Cancer J. Clin.*, 2004, 54, 8-29). During the period of 1992 to 1999, the average annual incidence of PCA among African American men was 59% higher than among Caucasian men, and the average annual death rate was more than twice that of Caucasian men (American Cancer Society—Cancer Facts and Figures 2003). Androgens play an important role in the development, growth, and progress'sion of PCA (McConnell, J. D., "Physiological basis of endocrine therapy for prostatic cancer", *Urol. Clin. North Am.*, 1991, 18: 1-13). The two most important androgens in this regard are testosterone (T) and dihydrotestosterone (DHT). The testes synthesize about 90% of T and the rest (10%) is synthesized by the adrenal glands. T is further converted to the more potent androgen DHT by the enzyme steroid 5α-reductase that is localized primarily in the prostate (Bruchovsky et al., "The conversion of testosterone to 5α-androstan-17β-ol-3-one by rat prostate in vivo and in vitro", *J. Biol. Chem.*, 1968, 243, 2012-2021). Huggins et al. introduced androgen deprivation as therapy for advanced and metastatic PCA in 1941 (Huggins et al. "Studies on prostatic cancer: 2. The effects of castration on advanced carcinoma of the prostate gland.", *Arch. Surg.*, 1941, 43, 209-212). Thereafter, androgen ablation therapy has been shown to produce the most beneficial responses in multiple settings in PCA patients (Denmeade et al. "A history of prostate cancer treatment." *Nature Rev. Cancer*, 2002, 2: 389-396). Orchidectomy (either surgical or medical with a GnRH agonist) remains the standard treatment option for most prostate cancer patients. Medical and surgical orchidectomy reduces or eliminates androgen production by the testes but does not affect androgen synthesis in the adrenal glands. Several studies have reported that a combination therapy of orchidectomy with antiandrogens, to inhibit the action of adrenal androgens, significantly prolongs the survival of PCA patients (Crawford, et al., "A controlled trial of leuprolide with and without flutamide in protatic carcinoma", *N. Engl. J. Med.*, 1989, 321, 419-424; Crawford, et al., "Treatment of newly diagnosed state D2 prostate cancer with leuprolide and flutamide or leuprolide alone, Phase III: intergroup study 0036 ", *J Urol.*, 1992, 147: 417A; and Denis, L., "Role of maximal androgen blockade in advanced prostate cancer", *Prostate*, 1994, 5 (Suppl.), 17s-22s). In a recent featured article by Mohler and colleagues (Mohler et al., "The androgen axis in recurrent prostate cancer", *Clin. Cancer Res.*, 2004, 10, 440-448) it was clearly demonstrated that T and DHT occur in recurrent PCA tissues at levels sufficient to activate androgen receptor. In addition, using microarray-based profiling of isogenic PCA xenograft models, Sawyer and colleagues (Chen et al., "Molecular determinants of resistance to antiandrogen therapy." *Nat. Med.*, 2004, 10, 33-39) found that a modest increase in androgen receptor mRNA was the only change consistently associated with the development of resistance to antiandrogen therapy. Potent and specific compounds that inhibit androgen synthesis in the testes, adrenals, and other tissue may be more effective for the treatment of PCA (Njar, V. C. O.; Brodie, A. M. H., "Inhibitors of 17α-hydroxylase-$C_{17-20}$-lyase (CYP17): Potential agents for the treatment of prostate cancer", *Current Pharm. Design*, 1999, 5: 163-180).

In the testes and adrenal glands, the last step in the biosynthesis of T involves two key reactions, which act sequentially and they are both catalyzed by a single enzyme, the cytochrome P450 monooxygenase 17α-hydroxylase/17,20-lyase (CYP17) (Hall, P. F., "Cytochrome P-450 $C_{21scc}$: one enzyme with two actions: Hydroxylase and lyase", *J. Steroid Biochem. Molec. Biol.,* 1991, 40, 527-532). Ketoconazole, as an antifungal agent and by virtue of inhibiting P450 enzymes, is also a modest CYP17 inhibitor and has been used clinically for the treatment of PCA (Trachtenberg et al., "Ketoconazole: A novel and rapid treatment for advanced prostatic cancer", *J. Urol.* 1983, 130, 152-153). It is reported that careful scheduling of treatment can produce prolonged responses in otherwise hormone-refractory prostate cancer patients (Muscato et al., "Optimal dosing of ketoconazole and hydrocrtisone leads to long responses in hormone refractory prostate cancer", *Proc. Am. Assoc. Cancer Res.,* 1994, 13: 22 (Abstract)). Furthermore, ketoconazole was found to retain activity in advanced PCA patients with progression despite flutamide withdrawal (Small et al., "Ketoconazole retains activity in advanced prostate cancer patients with progression despite flutamide withdrawal", J. Urol., 1997, 157, 1204-1207). Although, ketoconazole has now been withdrawn from use because of liver toxicity and other side effects this suggests that more potent and selective inhibitors of CYP17 could provide useful agents for treating this disease, even in advanced stages and in some patients who may appear to be hormone refractory.

A variety of potent steroidal and non-steroidal inhibitors of CYP17 have been reported and some have been shown to be potent inhibitors of testosterone production in rodent models (Njar and Brodie, above). Recently, Jarman and colleagues have described the hormonal impact of their most potent CYP17 inhibitor, abiraterone in patients with prostate cancer (O'Donnell et al., "Hormonal impact of the 17α-hydroxylase/C17,20-lyase inhibitors abiraterone acetate (CB7630) in patients with prostate cancer", *Br. J. Cancer,* 2004, 90: 2317-2325). Some of our potent CYP17 inhibitors have been shown to also inhibit 5α-reductase and/or are potent antiandrogens with potent antitumor activity (Njar and Brodie, above, and Long et al., "Antiandrogenic effects of novel androgen synthesis inhibitors on hormone-dependent prostate cancer." *Cancer Res.,* 2000, 60, 6630-6640). $C_{17-20}$-lyase catalyzes both the 17α-hydroxylation and the cleavage of the $C_{17,20}$-side chain during the conversion of the 21-carbon steroids pregnenolone and progesterone to the 19-carbon androgens dehydroepiandrosterone and androstenedione, respectively. Further illustrative of the background of the invention are U.S. Pat. Nos. 5,994,335; 6,200,965; and, 6,444,683.

We have discovered a series of potent CYP17 inhibitors/antiandrogens, the 17-benzoazoles, 17-pyrimidinoazoles and 17-diazines (see, e.g., Schemes 1 and 2, for examples of preparation of compounds which can be analogously applied to other structures, as described below). The stimulus for preparing these C-17 heteroaryl steroids was based on our desire to incorporate benzimidazole, benzotriazole, pyrimidinoazole and diazine moieties, so-called "privileged substructures" (Nicolaou et al., "Natural product-like combinatorial libraries based on privileged structures. 1. General principles and solid-phase synthesis of benzopyrans", *J. Am. Chem. Soc.,* 2000, 122, 9939-9953. *"Privileged structures"*, a term originally introduced by Evans et al. (*J. Med. Chem.,* 1988, 31, 2235-2246) to describe structural motifs capable of interacting with a variety of unrelated molecular targets) in the new molecules. These scaffolds, especially the benzimidazole scaffold, continue to receive extensive attention in medicinal chemistry because of their diverse portfolio of biological activities and also as entities of a variety of useful drugs (Nicolaou et al., above).

The C-17 heteroaryl steroid compounds of the invention are of the following general formula I:

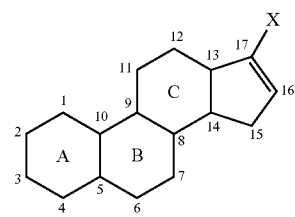

wherein:
the ABC ring structure is the A, B and C ring portions of a steroid or analog thereof, which are optionally substituted;
the ⁻⁻⁻⁻ bond at the 16,17 position is a double bond or, when the compound is 17-(1H-benzimidiazol-1-yl)androst-3-one, a single bond; and
X is an optionally substituted benzimidazole, benzotriazole, pyrimidinoimidazole (purine), pyrimidinotriazole or diazine; the benzimidazole, benzotriazole, and pyrimidinoimidazole groups being bonded to the steroid residue through a nitrogen atom on the 5-membered ring; and, the diazine groups being bonded to the steroid residue through a carbon atom on the diazine ring.

Pharmaceutically acceptable salts of these compounds are also included in the invention.

The optional substitution for the ABC ring structure includes one or more of: alkyl and halogenated alkyl (preferably $C_{1-6}$); alkenyl and halogenated alkenyl (preferably $C_{1-6}$) including where the double bond is directly attached to the ring structure; halogen; amino; aminoalkylene; hydroxyimino; and hydroxy. Further optionally, hydrogen substituents on adjacent carbon atoms of the ABC ring structure may be removed and replaced by an additional bond between the adjacent carbon atoms to result in a double bond between these carbons in the ring structure. Preferred optional substitutions on the ABC ring structure are methyl groups at the 10 and/or 13 positions of the ring structure.

The optional substitution for the benzimidazole, benzotriazole, pyrimidinoimidazole, pyrimidinotriazole or diazine structures include halogen, amino, aminoalkylene, hydroxy, —SH, —S-alkyl, alkyl and halogenated alkyl (preferably $C_{1-6}$). These optional substituents will be on ring carbon atoms of the benzimidazole, benzotriazole, pyrimidinoimidazole, pyrimidinotriazole or diazine structures.

The benzimidazole, benzotriazole, pyrimidinoimidazole, pyrimidinotriazole or diazine structures are of the following formulae, respectively:

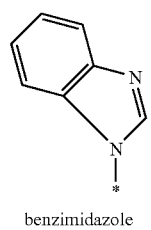

benzimidazole

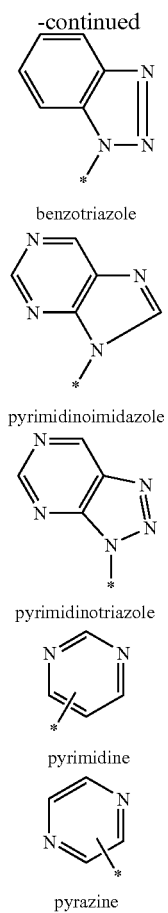

benzotriazole pyrimidinoimidazole pyrimidinotriazole pyrimidine pyrazine wherein the * indicates the point of attachment to the steroid residue.

In one preferred embodiment, the ABC ring structure has a C ring which has no substitution except for preferably alkyl, particularly methyl, substitution at the carbon shared with the D ring which is adjacent the attachment to the C-17 heteroaryl substitution, i.e., the 13-position.

In another preferred embodiment, the A, B and C rings of the ABC ring structure have a conventional structure based on 3β-hydroxy-androsta-5,16-diene or 3-oxo-androsta-5,16-diene. But in another embodiment the A and B rings have one of the following structures 1-25:

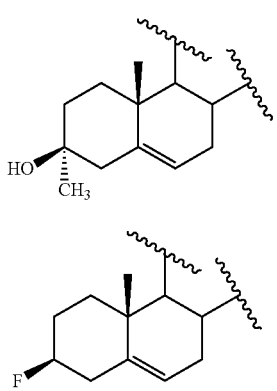

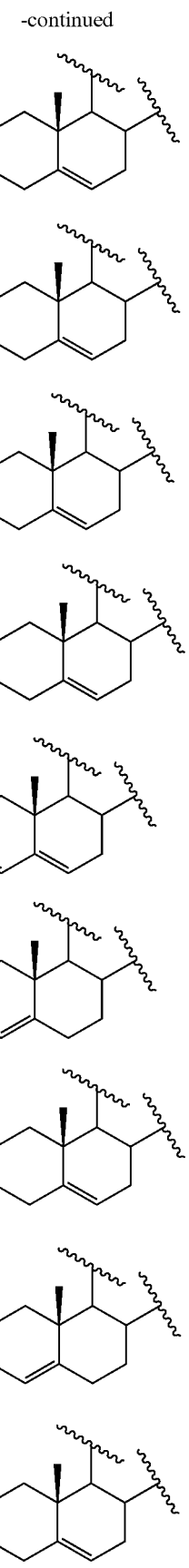

-continued

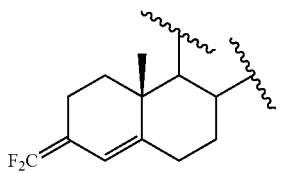
12

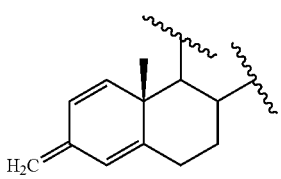
13

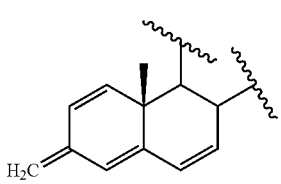
14

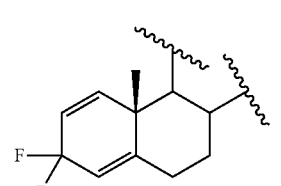
15

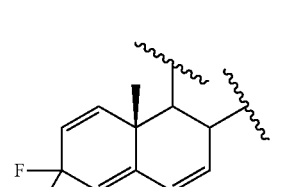
16

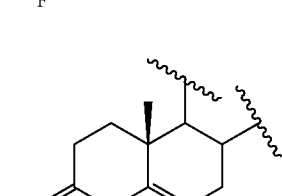
17

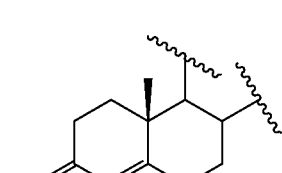
18

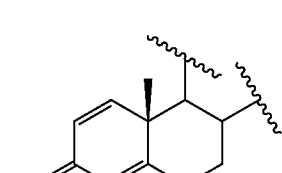
19

-continued

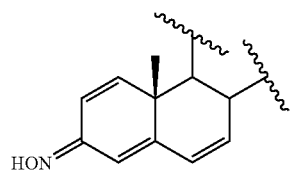
20

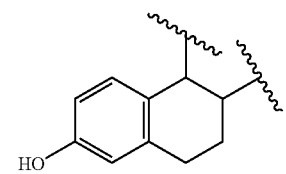
21

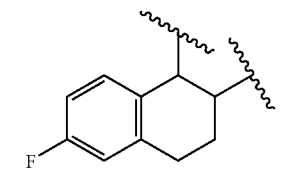
22

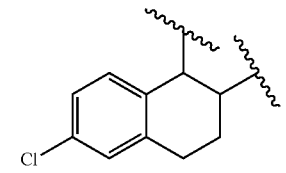
23

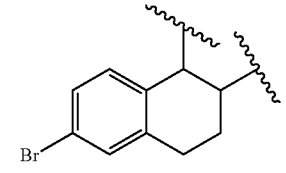
24

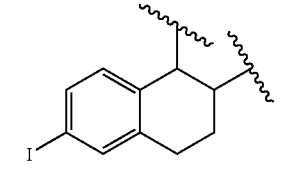
25

The following lists the chemical names of compounds having the AB rings as in 1-25, and the C and D rings conventional, wherein X is benzamidazole. Analogous compounds wherein X is benzotriazole, pyrimidinoimidazole, pyrimidinotriazole, pyrazine or pyrimidine are also contemplated.

| | |
|---|---|
| Compound 1: | 3β-Hydroxy-3α-methyl-17-(1H-benzimidazol-1-yl)-androsta-5,16-diene |
| Compound 2: | 3β-Fluoro-17-(1H-benzimidazol-1-yl)-androsta-5,16-diene |
| Compound 3: | 3β-Chloro-17-(1H-benzimidazol-1-yl)-androsta-5,16-diene |
| Compound 4: | 3β-Bromo-17-(1H-benzimidazol-1-yl)-androsta-5,16-diene |
| Compound 5: | 3β-Iodo-17-(1H-benzimidazol-1-yl)-androsta-5,16-diene |
| Compound 6: | 3β-Amino-17-(1H-benzimidazol-1-yl)-androsta-5,16-diene |
| Compound 7: | 17-(1H-benzimidazol-1-yl)-androsta-3,5,16-triene |
| Compound 8: | 17-(1H-benzimidazol-1-yl)-androsta-2,4,16-triene |
| Compound 9: | 17-(1H-benzimidazol-1-yl)-3-methyleneandrosta-5,16-triene |

-continued

| | |
|---|---|
| Compound 10: | 17-(1H-benzimidazol-1-yl)-3-methyleneandrosta-4,16-triene |
| Compound 11: | 3,3-Difluoro-17-(1H-benzimidazol-1-yl)-androsta-5,16-diene |
| Compound 12: | 3,3-Difluoro-17-(1H-benzimidazol-1-yl)-androsta-4,16-diene |
| Compound 13: | 17-(1H-benzimidazol-1-yl)-3-methyleneandrosta-2,4,16-triene |
| Compound 14: | 17-(1H-benzimidazol-1-yl)-3-methyleneandrosta-2,4,6,16-tetraene |
| Compound 15: | 3,3-Difluoro-17-(1H-benzimidazol-1-yl)-androsta-2,4,16-triene |
| Compound 16: | 3,3-Difluoro-17-(1H-benzimidazol-1-yl)-androsta-2,4,6,16-tetraene |
| Compound 17: | 3-Hydroxyimino-17-(1H-benzimidazol-1-yl)-androsta-5,16-diene |
| Compound 18: | 3-Hydroxyimino-17-(1H-benzimidazol-1-yl)-androsta-4,16-diene |
| Compound 19: | 3-Hydroxyimino-17-(1H-benzimidazol-1-yl)-androsta-2,4,16-triene |
| Compound 20: | 3-Hydroxyimino-17-(1H-benzimidazol-1-yl)-androsta-2,4,6,16-diene |
| Compound 21: | 3-Hydroxy-17-(1H-benzimidazol-1-yl)-estra-1,3,5(10),16-tetraene |
| Compound 22: | 3-Fluoro-17-(1H-benzimidazol-1-yl)-estra-1,3,5(10),16-tetraene |
| Compound 23: | 3-Chloro-17-(1H-benzimidazol-1-yl)-estra-1,3,5(10),16-tetraene |
| Compound 24: | 3-Bromo-17-(1H-benzimidazol-1-yl)-estra-1,3,5(10),16-tetraene |
| Compound 25: | 3-Iodo-17-(1H-benzimidazol-1-yl)-estra-1,3,5(10),16-tetraene |

Examples of optional substituents for the heteroaryl ring, X, are shown by the following structures 26-40 wherein X is benzimidazole. Analogous compounds wherein X is substituted benzotriazole, pyrimidinoimidazole, pyrimidinotriazole, pyrazine or pyrimidine are also contemplated.

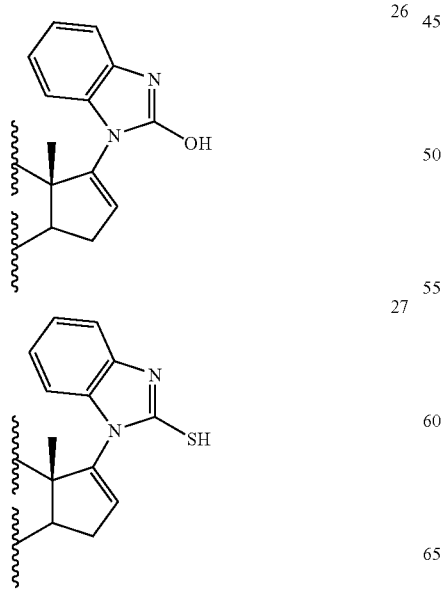

26

27

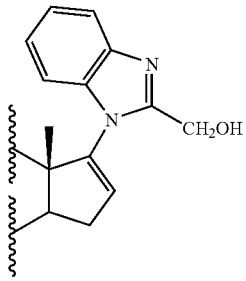

28

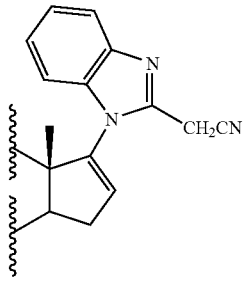

29

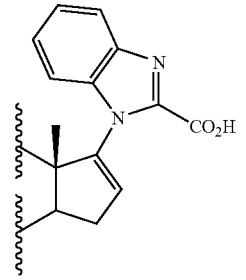

30

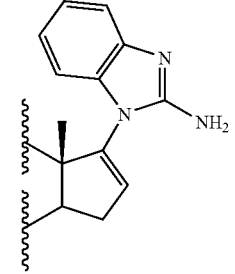

31

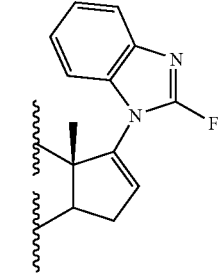

32

33
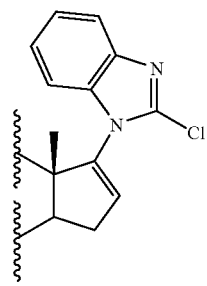
34
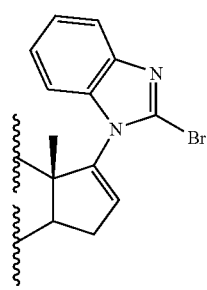
35
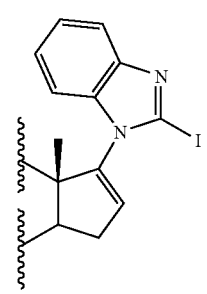
36
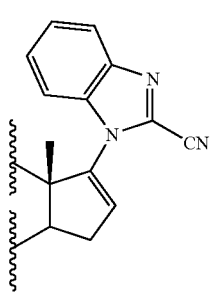
37
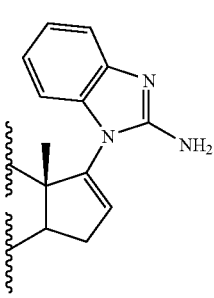
38
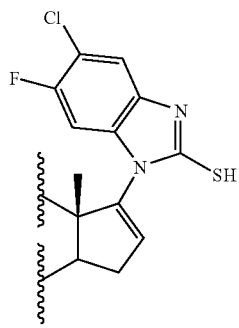
39
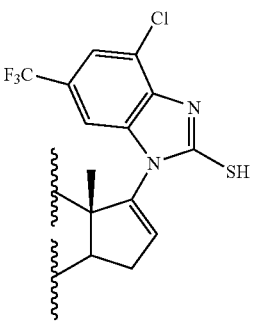
40
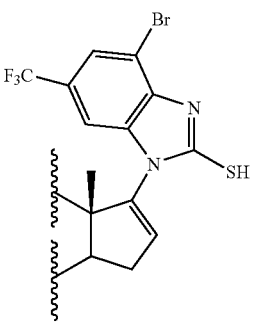
Other examples of optional substituents for the heteroaryl ring, X, are shown by the following structures 41-46 wherein X is substituted C-17-azabenzimidazole (i.e., pyrimidinoimidazole or purine). Analogous compounds wherein X is substituted benzimidazole, benzotriazole, pyrimidinotriazole, pyrazine or pyrimidine are also contemplated.
41
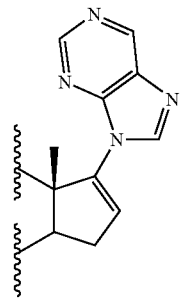

-continued

42
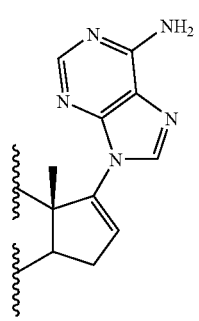

43
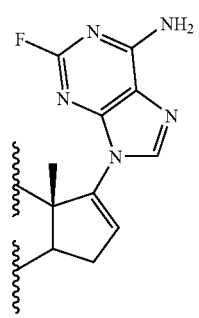

44
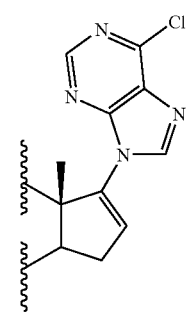

45
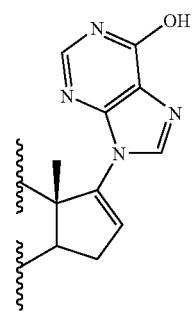

46
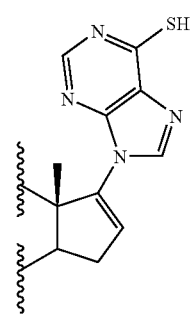

Particularly preferred compounds are those of the following structures M5, M6, M9 and M10.

M5
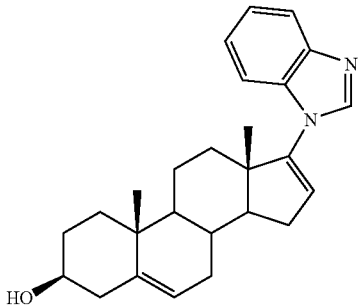

M6
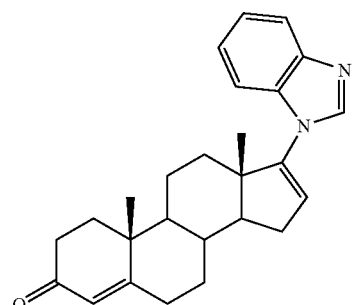

M9
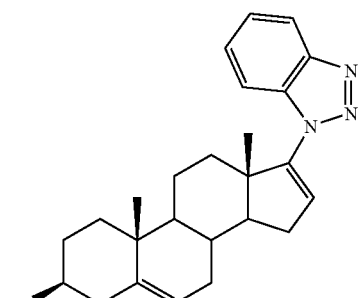

M10
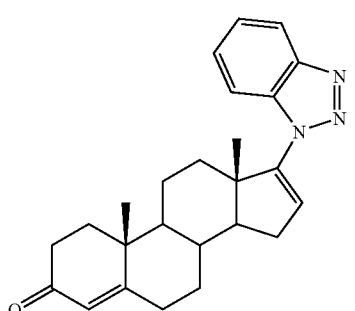

The inhibitory activities of these compounds compared to CYP17 and steroid 5α-reductases, the binding to and transactivation of androgen receptors, and their antiproliferative effects against two human prostate cancer cell lines, LNCaP and LAPC-4 were studied. The pharmacokinetics of compounds 5 and 6 were evaluated in mice and the in vivo antitumor activities against human LAPC-4 prostate carcinoma were also evaluated in mice. To our knowledge, all the compounds described here, with the exception of compound 15 represent novel entities (Haidar et al., "Novel steroidal pyrimidyl inhibitors of P450 17 (17α-hydroxylase/C17-20-lyase)", Arch. Pharm. Med. Chem., 2001, 334, 373-374; and Haidar et al., "Effects of novel 17α-hydroxylase/C17,20-lyase (P45017, CYP17) inhibitors on androgen biosynthesis in vitro and in vivo", J. Steroid Biochem. Molec. Biol., 2003, 84, 555-562).

The preparation of the new 17-benzoazoles and 17-diazines is outlined in Schemes 1 and 2, respectively. These methods can be applied analogously to other analogs described herein.

The key intermediate in our synthesis of the 17-benzazoles, 3β-acetoxy-17-chloro-16-formylandtrosta-5,16-dine (2) was obtained from (1) by our routine procedure as previously described (Njar et al., "Nucleophilic vinylic "addition-elimination" substitution reaction of 3β-acetoaxy-17-chloro-16-formylandrosta-5,16-diene: A novel and general route to 17-substituted-$\Delta^{16}$-steroids. Part 1. Synthesis of novel 17-azolyl-$\Delta^{16}$ steroids; inhibitors of 17α-hydroxylase/17,20-lyase (P450$_{17\alpha}$)", Bioorg. Med. Chem. Lett., 1996, 6, 2777-2782; and "Novel 17-azolyl steroids; potent inhibitors of cytochrome P450 17α-hydroxylase/17,20-lyase (P450$_{17\alpha}$): Potential agents for the treatment of prostate cancer", J. Med. Chem., 1998, 41, 902-912). Treatment of 2 with benzimidazole in the presence of $K_2CO_3$ in DMF at approximately 80° C. gave the desired 3β-acetoxy-17-1H-benzimidazole 3 in near quantitative yield. Compound 3 was smoothly deformylated with 10% palladium on activated charcoal in refluxing benzonitrile to give compound 4 in 93% yield, from which hydrolysis gave the required 3β-hydroxy 17-benzimidazole 5. Modified Oppenauer oxidation of 5 afforded the corresponding $\Delta^4$-3-oxo analog, 6.

The reaction of 2 with benzotriazole in the presence of $K_2CO_3$ in DMF at approximately 80° C. gave the desired 3β-acetoxy-17-benzo-1H-1,2,3-triazole 7b in excellent yield, together with the 2H-1,2,3-triazole regioisomer 7a in approx 5% yield. These two regioisomers were readily separated by flash column chromatography (FCC) on silica gel and were also easily identified by their respective proton NMR spectra. Thus, the four aromatic protons of the symmetrical 2H-1,2,3-triazole 7a appeared as two pairs of doublets at δ 7.43, 7.45, 7.88 and 7.90 while the four aromatic protons of the unsymmetrical 1H-1,2,3-triazole 7b appeared as multiplet at δ 7.46 (2H) and doublets at δ 7.57 (1H) and 8.15 (1H), respectively. In addition, the 16-CHO proton in 7a was significantly shifted downfield to δ 10.66 compared to that in 7b at δ 9.59. Deformylation of 7b with in situ generation of Rh(1,3-bis (diphenylphosphino)propane)$_2$$^+$Cl$^-$ catalyst [Rh(dppp)$_2$$^+$ Cl$^-$] in refluxing xylenes gave compound 8, and following hydrolysis of the 3β-acetoxy group, we obtained the target 3β-hydroxy-17-(benzo-1H-1,2,3-triazol-1-yl)androsta-5,16-diene (9) in 90% yield. Oxidation of 9 afforded 10 in good yield.

Synthesis of the 17-diazines, (17-diazine 14 and 17-pyrimidine 15) commenced from the readily available dehydroepiandrosterone (11, Scheme 2), which was converted to the corresponding 17 hydrazone 12 by treatment with hydrazine hydrate and hydrazine sulfate as previously described by Potter et al., A convenient, large-scale synthesis of abiraterone acetate [3β-acetoxy-17(3-pyridyl)androsta-5,16-diene], a potential new drug for the treatment of prostate cancer. Org. Prep. Proc. Int., 1997, 29, 123-128. Treatment of 12 with iodine in the presence of 1,1,3,3-tetramethylguanidine gave the vinyl 17-iodide 13 in excellent yield. The palladium catalyzed cross-coupling reactions (Choshi et al., "Total synthesis of Grossularines-1 and -2." J. Org. Chem., 1995, 60, 5899-5904) of 13 with (2-tributylstannyl)pyrazine or (5-tributylstannyl)pyrimidine proceeded to give 3β-hydroxy-17-(2-pyrazyl)-androsta-5,16-diene (14, 15%), and 3β-hydroxy-17-(5-pyrimidyl)-androsta-5,16-diene (15, 10%), respectively. The low yields of these two cross-coupling reactions may be due to instability of the stannyldiazine reagents under the reaction conditions employed. The structures of the target compounds, 14 and 15 were readily identified by their proton NMR spectra: The three nonequivalent protons of the 17-pyrazine moiety in 14 appeared as three singlets at δ 8.35, 8.48 and 8.70, while for the three protons of the 17-pyrimidine moiety in 15, two equivalent protons appear as a singlet at δ 8.73 and one proton appeared at δ 9.07. Furthermore, the 17-diazine groups of 14 and 15 exhibit different influences on the chemical shifts of their respective 16-olefinic protons with respect to the 16-proton of the precursor $\Delta^{16}$-17-iodide 13: the 16-H in 14 appeared as a singlet at δ 6.77, being significantly deshielded compared to the 16-H in 13 (δ6.14); the 16-H in 15 appeared at δ 6.11, similar to 13. As indicated above, compound 15 was previously reported Haidar et al., however, it was synthesized by a procedure that is different from the one described herein.

A representative sample of the novel compounds were then subjected to extensive in vitro and in vivo studies as described in detail in the following sections.

The present invention also relates to method of treating prostate cancer or prostate hyperplasia comprising administering to a subject in need thereof an effective amount of a compound in accordance with the present invention. The term "treating" is used conventionally, e.g., the management or care of a subject for the purpose of combating, alleviating, reducing, relieving, improving, etc., one or more of the symptoms associated with the prostate disease. Examples of prostate diseases that can be treated include, e.g., prostatic hyperplasia (BPH), and prostate cancer (e.g., prostatic adenocarcinoma).

The specific dose level and frequency of dosage may vary, depending upon a variety of factors, including the activity of the specific active compound, its metabolic stability and length of action, rate of excretion, mode and time of administration, the age, body weight, health condition, gender, diet, etc., of the subject, and the severity of the prostate cancer or hyperplasia. Any effective amount of the compound can be administered, e.g., from about 1 mg to about 500 mg per day, more specifically about 50 mg to about 150 mg per day. The compounds can be administered in any form by any effective route, including, e.g., oral, parenteral, enteral, intraperitoneal, topical, transdermal (e.g., using any standard patch), ophthalmic, nasally, local, non-oral, such as aerosol, spray, inhalation, subcutaneous, intravenous, intramuscular, buccal, sublingual, rectal, vaginal, intra-arterial, and intrathecal, etc. The composition may be in a unit dosage form. Typical unit dosage forms include tablets, pills, powders, solutions, suspensions, emulsions, granules, capsules, suppositories, injectable solutions and suspensions. A compound of the present invention can be administered alone, or in combination with any other ingredient(s), active or inactive, for example, with physiologically acceptable vehicles to make suitable pharmaceutical compositions.

The entire disclosure of all applications, patents and publications, cited herein and of U.S. Provisional Application No. 60/657,390, filed Mar. 2, 2005, is incorporated by reference herein.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLES

Biological Studies

CYP17 Inhibition Studies: A CYP17 inhibition assay is performed according to our previously reported procedure, in which intact cytochrome P450c17-expressing *E. coli* is used as the enzyme source (Grigoryev et al., "Cytochrome P450c17-expressing *Escherichia coli* as a first-step screening system for 17α-hydroxylase-C17,20-lyase inhibitors", *Anal. Biochem.;* 1999, 267, 319-330; and "Effects of new 17α-hydroxylase/C17,20-lyase inhibitors on LNCaP prostate cancer cell growth in vitro and in vivo", *Br. J. Cancer,* 1999, 81, 622-630. $IC_{50}$ values of the compounds are determined from dose-response curves and are listed in Table 1. The $IC_{50}$ values for ketoconazole, abiraterone (a CYP17 inhibitor in clinical trials (O'Donnell, above), Chart 1) and 3β-hydroxy-17-(1H-imidazole-1-yl)androsta-5,16-diene (VN/85-1, compound 16, Chart 1, believed to be the most potent CYP17 inhibitor (Njar et al., *Current Pharm. Design,* 1999, 5: 163-180; and *J. Med. Chem.,* 1998, 41, 902-912, above) are also determined in the same assay system for comparison. Some of the new 17-heterocycles exhibit potent inhibition of CYP17 with $IC_{50}$ values of 300-915 nM. The benzimidazoles, 5 and 6 are 4- to 6-fold more potent than the benzotriazoles 9 and 10. This result suggests that the electronic nature of the 17-heterocycle influence inhibitory activity. Furthermore, compounds with the $\Delta^5$-3β-ol functionality, 5 and 9 are at least 3-fold more potent than the corresponding analogs with $\Delta^4$-3-one functionality, 6 and 10, respectively. These results are in contrast to our previous results for the simple 17-azole CYP17 inhibitors. In that series of inhibitors, there is no marked difference in the inhibitory potencies between the $\Delta^5$-3β-ol azoles and the corresponding $\Delta^4$-3-one analogs (Njar et al., *J. Med. Chem.,* 1998, 41, 902-912, above). A possible explanation is that the bulkier benzoazoles bind differently at the active site of the enzyme such that the interaction(s) of the moiety at the 3-position is important for binding.

The binding of the substrate or inhibitory ligands to the heme component of some P450 cytochromes is investigated using UV-vis difference spectroscopy (Jefcoat C. R., "Measurement of substrate and inhibitor binding to microsomal cytochrome P450 by optical difference spectroscopy", *Methods Enzymol.,* 1978, 52, 258-279). This approach is extended following standard procedure previously reported by us (Njar et al., *Bioorg. Med. Chem. Lett.,* 1996, 6, 2777-2782; and *J. Med. Chem.,* 1998, 41, 902-912). Compounds 5 and 9 each induce a type II difference spectrum, indicating coordination of steroidal nitrogen (N-3 of benzimidazole or benzotriazole ring) to the heme iron of CYP17, with formation of low-spin iron. The peak positions for the Soret maximum for the enzyme complex with 5 and 9 (426 nM) is in agreement with available data for the binding of nitrogen ligands to CYP systems, and is also in agreement with our results with other 17-azolyl CYP17 inhibitors (Njar et al., *Bioorg. Med. Chem. Lett.,* 1996, 6, 2777-2782; and *J. Med. Chem.,* 1998, 41, 902-912). The interaction of the benzoazole nitrogen with the heme iron of CYP17 suggests bulk tolerance at the 17-position, because the binding affinities of 5 and 9 are identical to that of the less sterically demanding 16, with a 17-imidazole group.

Of the two 17-diazines tested, the 17-pyrimidine 15 with an $IC_{50}$ value of 500 nM is about 8-fold more potent than the 17-pyrazine 14 ($IC_{50}$=3810 nM). As with the benzoazoles, this result suggests that the electronic nature of the 17-heterocycle influence inhibitory activity. Finally, $IC_{50}$ values in the same assay system for ketoconazole, and abiraterone are evaluated (Table 1). The most potent compound in this series, 17-benzimidazole 5, exhibits about 4 and about 3-fold improvements in CYP17 inhibition over these compounds, respectively, although it is less potent than 16.

Inhibition of human 5α-reductase isozymes type 1 and 2 in vitro: On the basis of previous findings that some CYP17 inhibitors are able to inhibit human 5α-reductase enzymes, we briefly evaluated this new series of CYP17 inhibitors. The inhibitory activities of compounds 5, 6, 9, 10 and finasteride as a reference are determined using the DU-145 cell line (human type 1 enzyme) and human homogenates of BPH tissue (human type 2 enzyme) as described by Hartmann et al., "Synthesis and evaluation of 2'-substituted 4-(4'-carboxy- or 4'-carboxymethylbenzylidene)-N-acylpiperidines: Highly potent and in vivo active steroid 5α-reductase type 2 inhibitors", *J. Med. Chem.,* 2002, 45, 3406-3417. The $IC_{50}$ values or the percent inhibition values at a concentration of 10 μM for some compound are presented in Table 1. Only compound 6 exhibits potent inhibition of both type 1 and 2 enzymes ($IC_{50}$=770 and 480 nM, respectively), although it is several fold less potent than finasteride ($IC_{50}$=60 and 2 nM, respectively).

LNCaP and PC-3AR androgen receptor binding assays: Because we had previously demonstrated that some of our CYP17 inhibitors are potent antiandrogens for both the mutant and wild-type AR (Long et al., Gregoriyev et al. and Njar et al., *J. Med. Chem.,* 1998, 41, 902-912, above) it was of interest to assess the ability of this series of CYP17 inhibitors to bind to these receptors. AR competition is determined using labeled R1881 ([$^3$H]-R1881) in the androgen-sensitive LNCaP cells, that express mutant AR, and the androgen-independent PC-3 cells stably transfected with the wild-type AR (designated PC-3AR). Compounds 5, 6, 14 and 15, in the nanomolar concentration range, compete effectively with labeled R1881 for binding to both types of ARs in a dose-dependent manner (Figure not shown). Compounds 5, 6, 14 and 15, with $IC_{50}$ values of 384, 242, 336 and 374 nM, respectively (Table 1), versus the wild type AR are 29 to 45-fold more potent than with the clinically used antiandrogen, flutamide ($IC_{50}$=10,985 nM). As shown in Table 1, the binding affinities for the mutant AR of 5 and 6 are comparable to that of casodex, a currently used antiandrogen, but again superior to that of flutamide. However, the biological activity of flutamide is derived mainly from a metabolite, hydroxyflutamide, which is a much more potent AR antagonist.

Effects of agents on LNCaP mutant AR-mediated transcription: Next, we asked whether compounds 5 and 6 are acting as AR agonists or antagonists. A study on androgen-regulated transcriptional activation is performed in LNCaP cells transiently transfected with a probasin luciferase reporter construct AARz-Luc (luciferase activity assay) (Kim et al., "Synergism of cytoplasmic kinases in IL6-induced ligand-independent activation of androgen receptor in prostate cancer cells", *Oncogene,* 2004, 23:1838-1844; and Zhang et al., "A Small composite probasin promoter confers high levels of prostate-specific gene expression through regulation by androgens and glucocorticoids in Vitro and in Vivo", *Endocrinology,* 2000, 141: 4698-4710). Compounds 5, 6 or casodex each at 0.1 and 10.0 μM have no effect on luciferase activity, whereas luciferase expression is increased approximately 99.6-fold after treatment with 1.0 nM DHT for 18 h (FIG. 1). Furthermore, luciferase expression induced by exposure to 1.0 nM DHT is decreased in a concentration-dependent manner by 5, 6, and casodex and in a similar fashion (FIG. 1). Together, these results suggest that compounds 5 and 6 like casodex do not possess AR agonistic or partial agonistic activity and may be considered as strong, pure androgen antagonists. Although we did not test the compounds with PC-3AR/LU cells, which express wild-type AR, it is likely that they may also behave in a similar fashion. We has previously shown that some of our CYP17 inhibitors were more comparable to casodex than to flutamide (Long et al., above), and this appears to be the case with these new compounds. In general, our novel compounds interact strongly with both AR types, an indication that the compounds may be useful for the treatment of patients with tumors expressing either wild-type or mutated AR, or for patients with amplified AR expression.

Figure 2A:
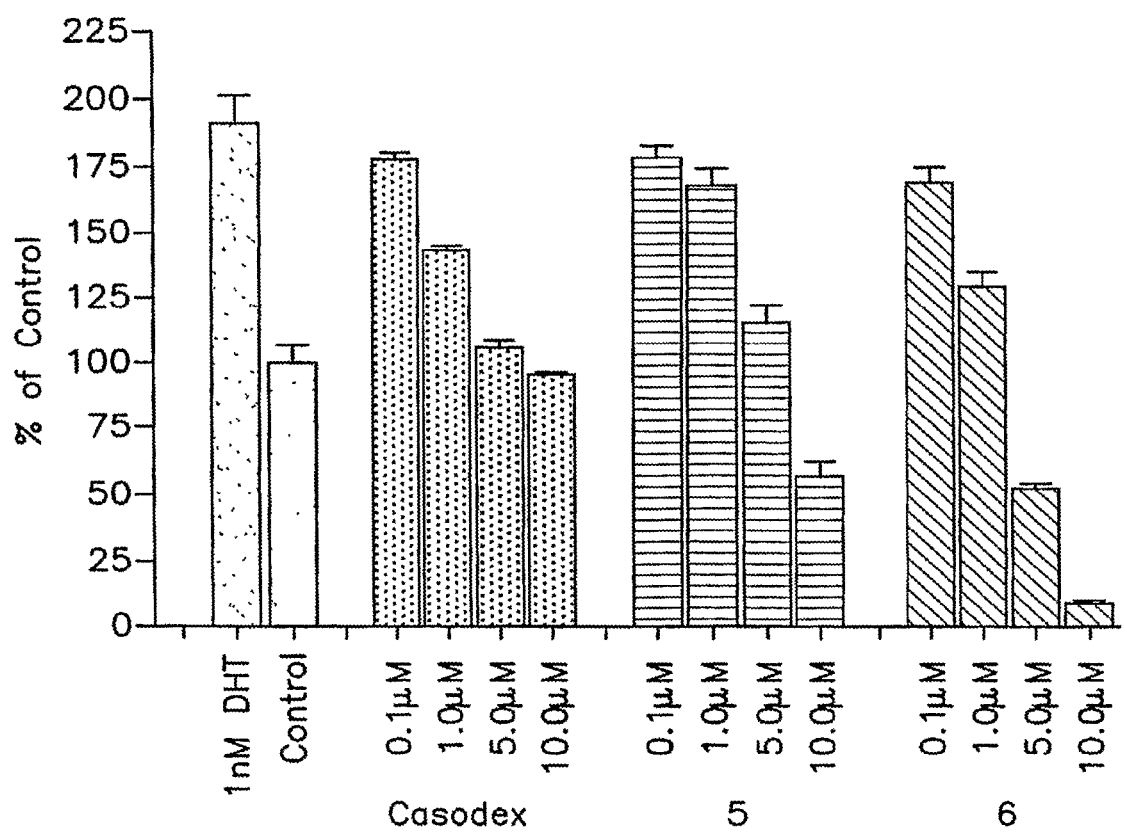
Figure 2B:
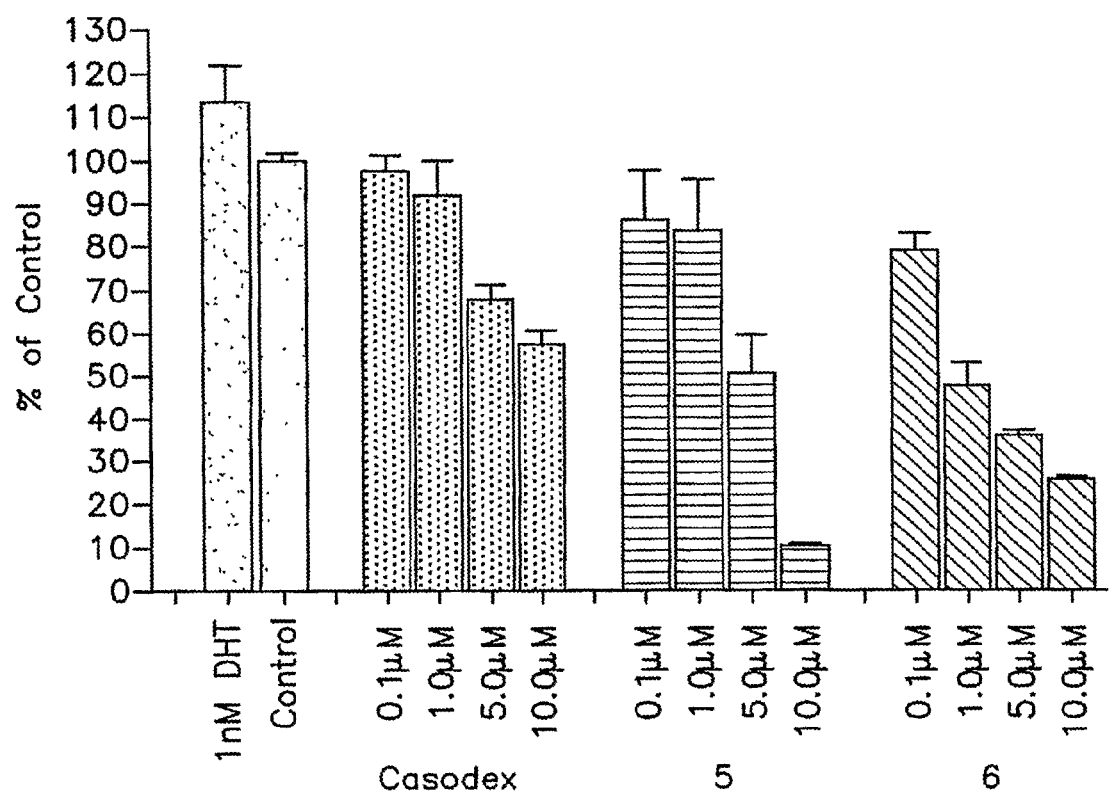

Effects of benzoazoles on the growth of LNCaP and LAPC-4 prostate cancer cells in vitro: The abilities of compounds 5 and 6 to inhibit proliferation in mutant LNCaP cells stimulated by 1 nM DHT is examined. This concentration of DHT stimulated LNCaP cell proliferation by about 2-fold compared to vehicle-treated cells (FIG. 2A). As shown in FIG. 2A, compounds 5 and 6 each inhibit the DHT-induced LNCaP cell proliferation in a dose-dependent fashion, with $IC_{50}$ values of 6.0 and 1.8 µM, respectively. Casodex is used as a positive control, and it exhibits similar inhibition of DHT-induced LNCaP cell proliferation (FIG. 2A, $IC_{50}$=8.6 µM). Treating the androgen-sensitive LAPC4 prostate cell line with 10 nM DHT, surprisingly, does not significantly induce cell proliferation (FIG. 2B). Other investigators have also reported that the response of LAPC4 cells to androgens is not as pronounced as that observed in LNCaP cells (Thompson et al., "Androgen antagonist activity by the antioxidant moiety of vitamin E, 2,2,5,7,8-pentamethyl-6-chromanol in human prostate carcinoma cells", *Molec. Caner Thera.*, 2003, 2, 797-803). However, compounds 5, 6 and casodex each exhibit a dose-dependent inhibition of this cell line (FIG. 2B) as with the LNCaP cells. The order of inhibitory potency of LAPC4 cell proliferation is 6>5>casodex, with $IC_{50}$ values of 1.0, 3.2 and 10 µM, respectively. Together, these results suggest that 5 and 6 may be acting to block the action of DHT in stimulating cell proliferation, in correlation with their androgen receptor binding and activation properties described above. Compounds 5 and 6 are amongst the most potent antiandrogens described to date.

Pharmacokinetics of 5 and 6 and metabolism of 5: The pharmacokinetic properties in male SCID mouse for the two lead compounds, 5 and 6 are studied following our recently described procedure for other CYP17 inhibitors (Nnane et al., "Pharmacokinetic profile of 3β-hydroxy-17-(1H-123-triazol-1-yl)androsta-5,16-diene (VN/87-1), a potent androgen synthesis inhibitor in mice", *J. Steroid Biochem. Molec. Biol.*, 2001, 71, 145-152; and Handratta et al., "Potent CYP17 inhibitors: improved syntheses, pharmacokinetics and antitumor activity in the LNCaP human prostate cancer model", *J. Steroid Biochem. Molec. Biol.*, 2004, 92, 155-165. The results are summarized in Table 2 and FIGS. 3-5.

Figure 3:
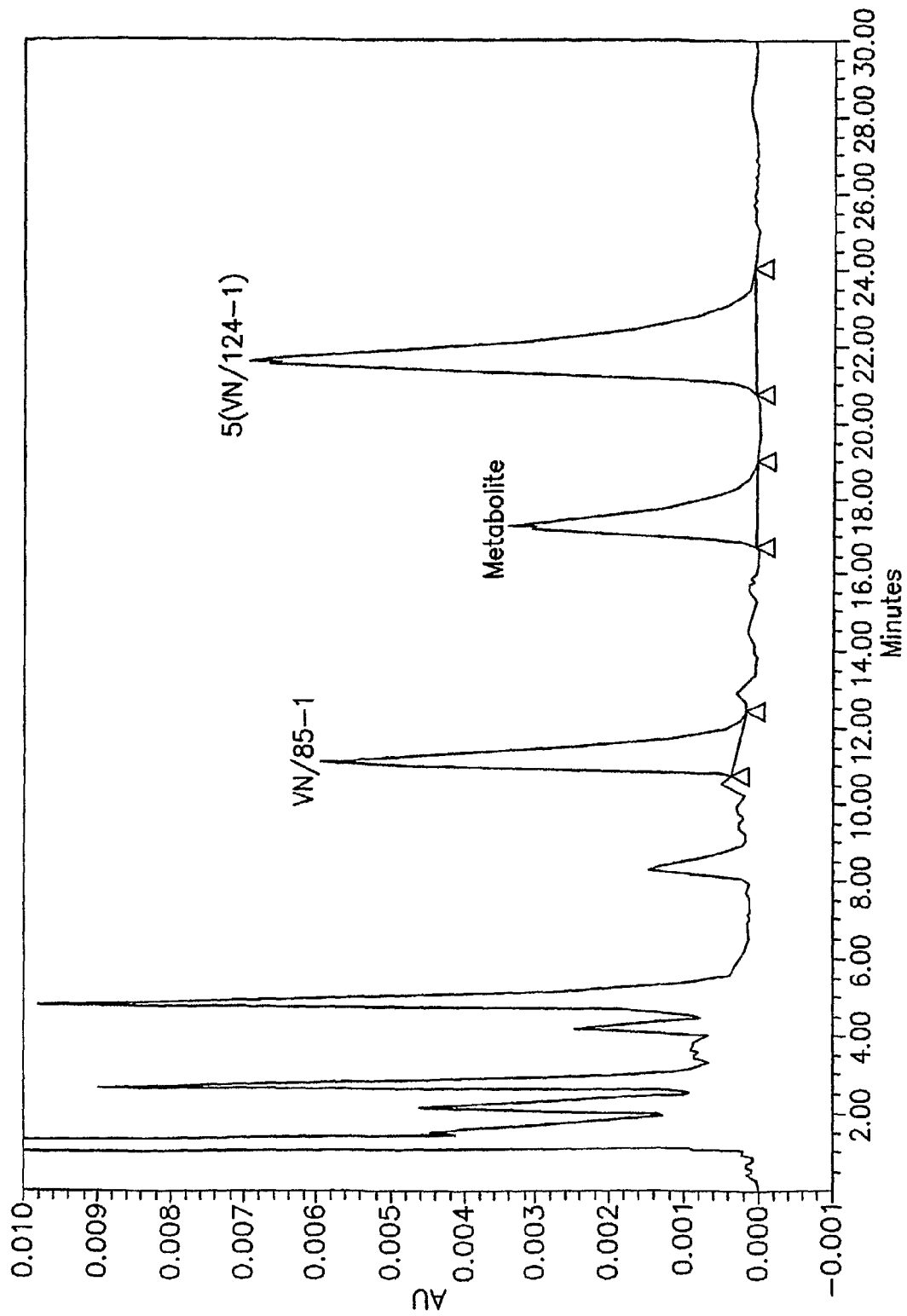

On reverse phase HPLC, 5 [retention time (rt)=21.6 min] is well resolved from the internal standard (16, rt=11.5 min), a metabolite (rt=17.3 min) and other endogenous compounds in mouse plasma (FIG. 3). The calibration curves derived for 5 are linear and reproducible (data not shown), the inter- and intra-assay variability is less than 10% and its limit of detection is 100 ng/ml. The HPLC assay is validated and used to monitor 5 in mice plasma.

Figure 4:
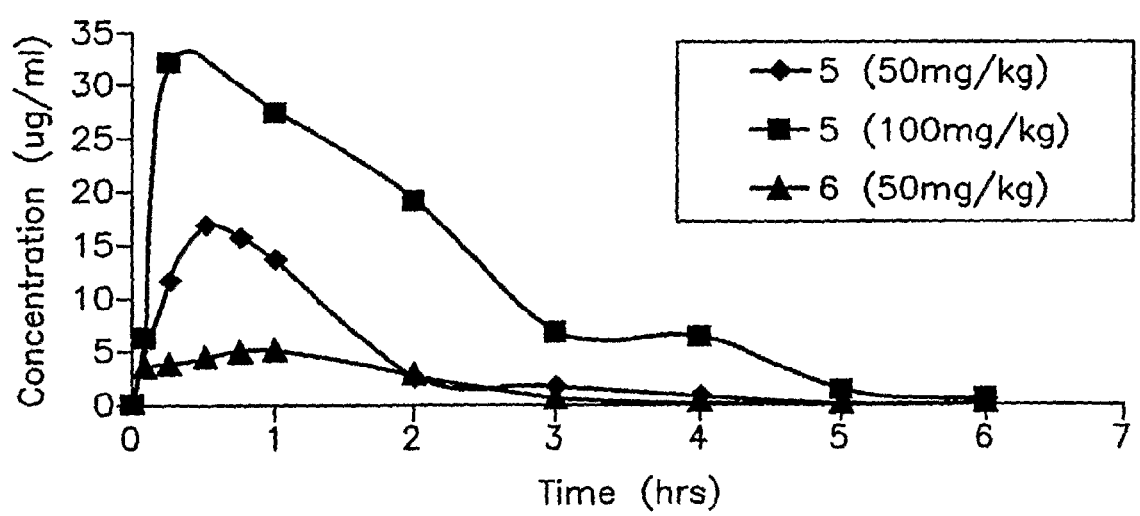

Following subcutaneous administration, the plasma concentration of 5 declines exponentially with a mean half-life of about 44.17 min and elimination rate constant of 56.5 $min^{-1}$. Compound 5 is cleared at a rate of 1986.14 ml/h/kg from the systemic circulation and was not detected 6 h after administration. The calculated non-compartmental pharmacokinetic parameters based on the plasma concentration profile following subcutaneous administration of 5 are shown in Table 2. The plasma concentration-time curves after s.c. administration of 5 (50 and 100 mg/kg) to male SCID mice are also shown in FIG. 4. After s.c. administration of 5, the observed plasma concentration in mice reach peak levels 30.0 min post dose. Compound 5 is well absorbed from the subcutaneous site and the area under the curve for the plasma concentration versus time profiles after s.c. administration increases proportionately to dose as the administration dose is changed from 50 to 100 mg/kg. Furthermore, the elimination half-life, and mean residence time are relatively constant as the dose of 5 increases from 50 to 100 mg/kg (Table 1). These results indicate that the pharmacokinetic profile of 5 is dose independent.

Figure 5:
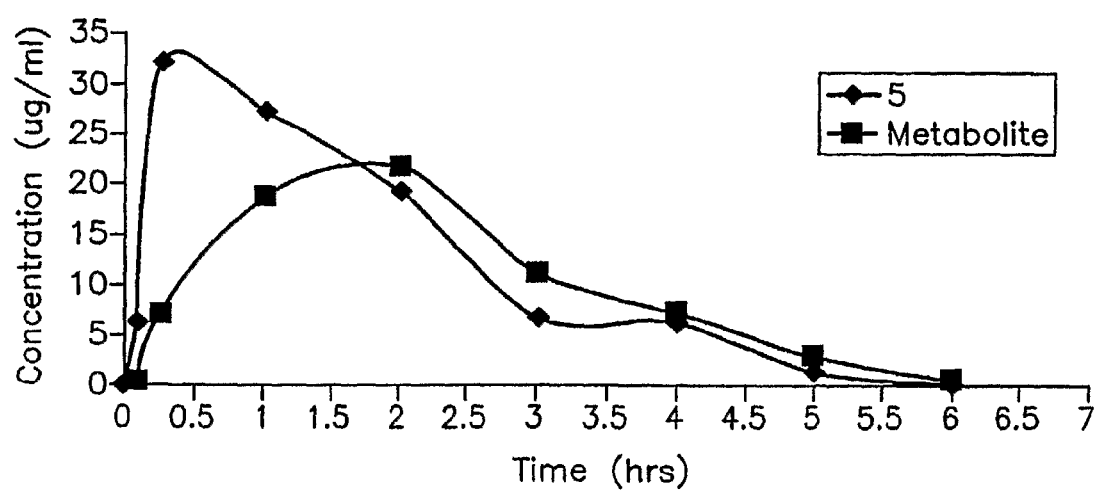

FIG. 5 shows that a significant amount of a polar metabolite [retention time, 17.3 min, see FIG. 3)] is formed from 5 and present in the plasma during the in vivo pharmacokinetic studies. The maximum amount of the metabolite is 67.72%, attained about 2 h post dose. This metabolite shows identical retention time as compound 6. This metabolite is tentatively identified by LC-MS; its molecular mass (m/z 391=M+H$^+$) is consistent with the structure of 3-oxo-$\Delta^{5,16}$-tetrahydro compound 5 (i.e., 17-(1H-benzimidazol-1-yl)androst-3-one). The metabolite may have been formed from 5 via oxidation of the 3β-OH→3-oxo, followed by reduction (reductases) of both $\Delta^5$ and $\Delta^{16}$ double bonds. A similar metabolite was previously identified (formed as a result of oxidation of a 3β-OH→3-oxo, followed by isomeraization of $\Delta^5$ double bond) in male mice of a closely related steroidal 17-imidazole (Handratta et al., above).

A major metabolite of 5, i.e., 17-(1H-benzimidiazol-1-yl) androst-3-one, may be synthesized from trans-androsterone; see Scheme 3. It is also expected to have analogous activity.

The in vivo pharmacokinetics of 6 in mice is unlike that of compound 5 due to the relatively low $C_{max}$ and significantly higher elimination rate (FIG. 4 and Table 2). In addition, we did not detect any metabolism(s) of compound 6 in the plasma, in contrast to our observation with compound 5.

Effects of 5 and 6 on LAPC4 Xenografts grown in SCID mice: On the basis of impressive multiple in vitro biological activities, i.e., potent inhibition of CYP17, strong antiproliferative prostate cancer cell activity and antiandrogenic activities, 5 and 6 are selected for in vivo antitumor efficacy studies in androgen-depended LAPC4 human prostate cancer xenograft model.

In the first experiment, the effect of compounds 5 and 6 on the growth of well-established LAPC4 prostate cancer tumors in SCID mice is determined, and castration is used as the reference treatment. Tumor-bearing mice are assigned (n=5/group) to receive one of two doses of 5 or 6 (0.15 mmol/kg once-daily or 0.15 mmol/kg twice-daily). Tumor volumes are measured weekly and compared with controls receiving vehicle or castrated mice.

Figure 6:
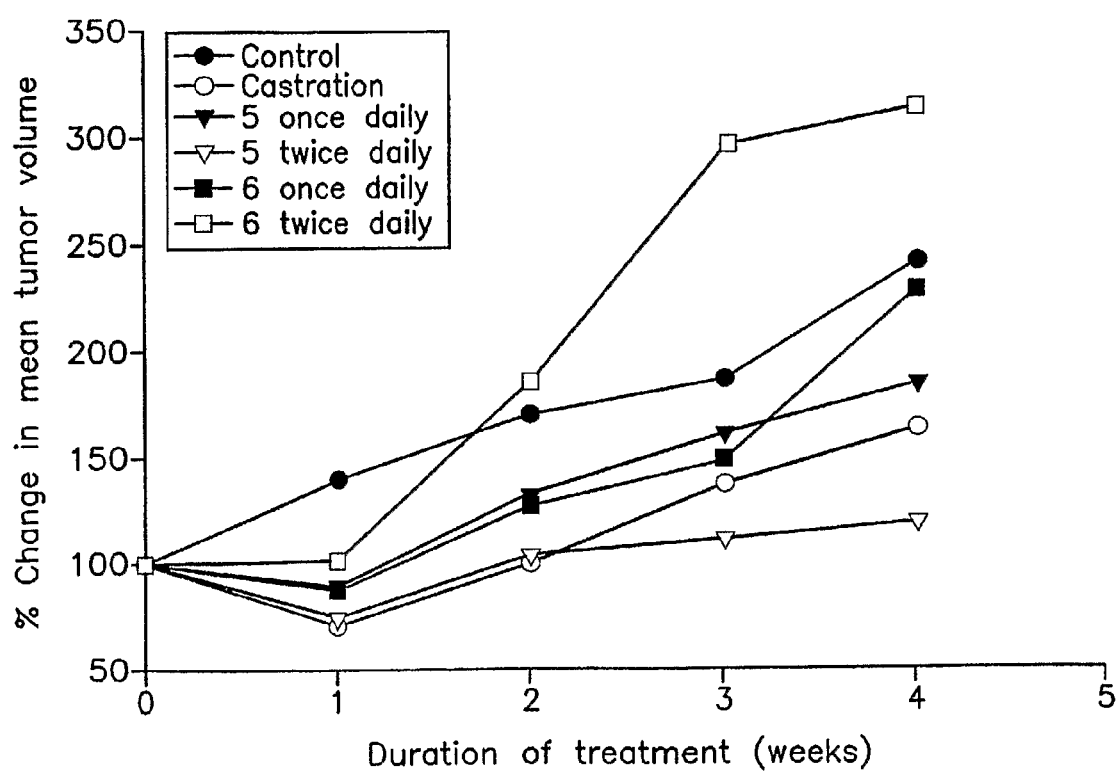

Castration leads to a 55% reduction of final tumor volume, as compared to the control (FIG. 6). Administration of 0.15 mmol/kg once daily and 0.15 mmol/kg twice daily of 5 results in reduction of average final tumor volumes of 41% and 86.5%, respectively, compared to tumors in vehicle-treated control animals (FIG. 6). In contrast to the excellent tumor growth inhibition for 5 treated mice, mice treated with compound 6 are either ineffective at the low dose or even show stimulation of tumor growth compared to control (FIG. 6). The inability of 6 to inhibit LAPC4 tumor growth in vivo is especially disappointing because the compound is very effective at inhibiting PCA cell growth in vitro, and is a highly potent pure antiandrogen (see FIG. 1). The highly significant disparity in the in vivo antitumor efficacy of 5 and 6 cannot easily be attributable to differences in the pharmacokinetic properties of the two compounds. The underlying reason(s) for the dramatic differences in in vivo antitumor efficacy of these two closely related compounds is unknown at this time. However, it may be attributable to 6 being converted in the animals to metabolite(s) that may be a strong agonist of androgen receptor thus causing tumor growth stimulation. During the study, all mice were weighed once per week. The body weights of all treated groups increased slightly and were similar to the increase observed with the control group. All mice appeared healthy and no adverse effects were observed suggesting that the compounds were without significant toxicity.

Figure 7:
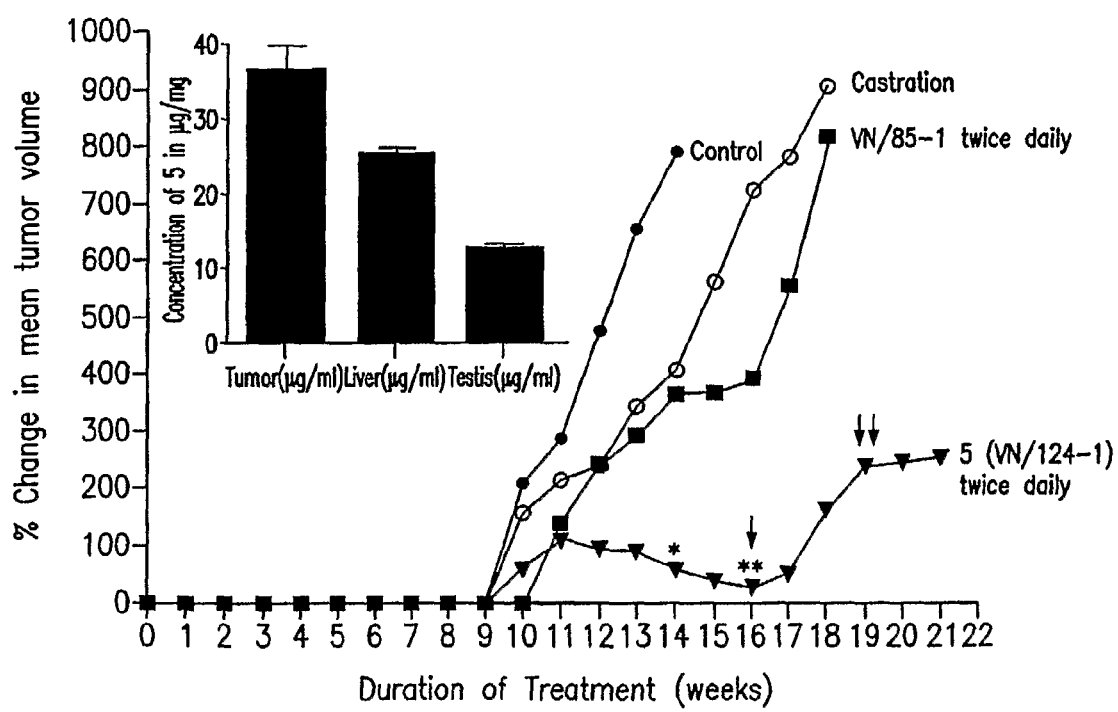

The second in vivo experiment tests the ability of 5 to inhibit the growth of LAPC4 prostate cancer cells growing in SCID mice, and 16 (Chart 1), a previously identified potent CYP17 inhibitor/antiandrogen (Gregoriyev et al. and Njar et al., *J. Med. Chem.*, 1998, 41, 902-912, above) and castration are used as reference treatments. In this experiment, treatment begins on the day that mice were inoculated subcutaneously with hormone-dependent LAPC4 cells and are castrated or injected sc twice daily with 5 or 16. FIG. 7 shows the effects of the various treatments on the emergence and on the size of tumors during the 21 weeks of therapy.

All other groups develop palpable and measurable tumor at week 10 of therapy except for the group treated with 16 (0.15 mmol/kg twice-daily) that develop palpable and measurable tumors at week 11. Total tumor volume in the control mice increases by 8-fold over 14 weeks of treatment when mice are sacrificed because of the large tumors. Thus, the tumor volumes for the other groups are compared to those of the control group at week 14 of treatment. Tumor volume in the castrated mice increases by only 4.1 fold (about 50% reduction compared to control), and is similar to the 3.7 fold increase (53.8% reduction compared to control) observed in mice treated with 16. In the mice treated with 5 (0.15 mmol/kg twice-daily), tumor volume increases by only 0.5 fold, which represents a 93.8% reduction versus control mice (P=0.00065). At week 16, the mean tumor volume in the compound 5-treated animals is found to be lower (almost negligible and dormant) than their mean tumor volume at week 10 when measurable tumors emerge. Furthermore, 5 causes a significant inhibitory effect on tumors, compared to 16 or castration, P=0.005 and 0.05, respectively. In general, tumors in the control, castration and compound 16 treated mice grow rapidly, while the tumor of the 5 treated mice grows very slowly and in a biphasic manner (FIG. 7). Compound 5 is the most effective agent, and significantly is much more effective than castration at inhibition of tumor growth. It is interesting to note that although 16 is 6 times more potent than 5 in CYP17 inhibition, the latter exhibits a superior in vivo antitumor activity. The reason(s) responsible for this phenomenon is unknown at this time, but may be in part due to better pharmacokinetic and or pharmacodynamic properties of 5.

To determine whether the "dormant" compound 5-treated prostate tumors (see FIG. 7, week 16) are able to grow on a lower dose of 5, its dose was reduced to 0.15 mmol/kg thrice a week (a 78.6% reduction in dosage) from weeks 16-19, and the tumor volumes measured weekly. During this period of treatment with reduced dose of the compound, tumors resume growth (FIG. 7). After this 3-week interval, drug treatment with the usual dose is resumed, and the tumor growth slows and reaches a plateau. These data suggest a cytostatic nature of this treatment and infer the need for continuous administration to achieve the antitumor effect.

At the end of the experiment, the levels of 5 in the tumors and organs of the 5-treated mice are determined. The 5 levels by HPLC in the tumors, testis and liver 1 h after administration of the final dose (insert of FIG. 7) are measured. Interestingly, a small (~15% relative to 5) amount of metabolite is detected only in the liver tissues. This metabolite has the same retention time as the metabolite observed in the plasma (vide supra). The highest concentration of 39.0±8.4 µg/mg tissue of 5 is measured in the s.c. tumors. The concentrations in the liver and testis are lower but detectable. The level of 5 in tumors is significantly higher that the levels measured in the plasma, which may be a result of accumulation of the compound through the period of the experiment. Thus, inhibition of tumor growth by 5 can be explained in part higher concentrations in tumor xenografts, which may exert direct cytotoxic/cytostatic effect on the prostate cancer cells. It should be stated that there is evidence to suggest a possible direct cytotoxic effect of ketoconazole (a modest CYP17 inhibitor) on prostate cancer cells.[33] In addition; the accumulation of 5 in the testes would enable inhibition of testosterone synthesis in the animals.

Although it is well established that LAPC4 are androgen-dependent, these cells can become androgen-independent, and as such represent a suitable model that mimics prostate cancer development in patients (Chen et al., above, and Kline et al., "Progression of metastatic human prostate cancer to androgen independence in immunodeficient SCID mice." *Nat. Med.*, 1997, 3, 402-408). As shown in FIG. 7, we are able to replicate this phenomenon. Furthermore, our results show that treatment with 16 or castration effectively suppresses tumor growth for a certain period (androgen-dependent phase), but was ineffective thereafter (possibly as a result of an androgen-independent phase) since the tumors grow rapidly just as in intact control mice. Tumor growth in the mice treated with 5 is strongly suppressed throughout the treatment period. This suggests that 5 may have effects on androgen-independent prostate cancer. However, it is also plausible that treatment with this compound enables LAPC4 tumors to remain androgen dependent for a longer period and therefore responsive to antiandrogen therapy.

Recent studies that clearly demonstrate the up-regulation and involvement of AR in advanced and recurrent PCA (Mohler et al., and Chen et al., above) have renewed interest in the androgen receptor as a target for development of drugs to treat PCA (Tindall et al., "Symposium on androgen action in prostate cancer", *Cancer Res.*, 2004, 64, 7178-7180). Because of its potent properties, 5 may be an excellent candidate.

Conclusions:

The data reinforce our earlier concept of modification of the C17 substituent of $\Delta^{16}$ steroids to produce potent inhibitors of CYP17 as well as potent AR antagonists. The 17-benzimidazoles 5 and 6 are shown to coordinate the heme iron of CYP17, a property that may in part be responsible for their enzyme inhibitory activity. Compounds 5 and 6 exhibit almost equipotent in vitro activities for CYP17 inhibition, AR antagonism, and inhibition of prostate cancer cell growth. Surprisingly, the compounds are very different in their anti-tumor activities, as 5 causes marked suppression of LAPC4 tumor xenograft growth, and in contrast, 6 (0.15 mmol/kg twice daily) enhances tumor growth. The present study provides compelling evidence that 5 is a potent inhibitor of human prostate tumor growth and is remarkably more effective than castration. This is the first example of a CYP17 inhibitor/antiandrogen demonstrating in vivo antitumor activity against a prostate cancer tumor to an extent that is superbly more effective than castration. These impressive biological activities, makes 5a strong candidate for further development as a potential drug for the treatment of prostate cancer in humans. The excellent antitumor activity of compound 5, containing a benzimidazole group makes the benzimidazoles a preferred group. However, analogs of 5 as discussed above are expected to have related activity and are included in the invention.

Experimental Section

Chemistry: General procedures and techniques were identical with those previously reported (Njar et al., *J. Med. Chem.*, 1998, 41, 902-912). Infra red spectra are recorded on a Perkin Elmer 1600 FTIR spectrometer using solutions in $CHCl_3$. High-resolution mass spectra (HRMS) are determined on a 3-Tesla Finnigan FTMS-2000 FT mass spectrometer, ESI mode (Ohio State University, Department of Chemistry). As a criterion of purity for key target compounds, we provided high resolution mass spectral data with HPLC chromatographic data indicating compound homogeneity. Low-resolution mass spectra (LRMS) are determined on a Finnegan LCR-MS. Melting points (mp) are determined with a Fischer Johns melting point apparatus and are uncorrected. Dehydroepiandrosterone and dehydroepiandrosterone acetate were purchased from Aldrich, Milwaukee, Wis. 5-Tributylstannylpyrimidine and 2-tributylstannylpyrazine were purchased from Frontier Scientific, Inc., Logan, Utah.

3β-Acetoxy-17-chloro-16-formylandrosta-5,16-diene (2): This compound prepared from 3β-acetoxyandrost-5-en-17-one (1) as previously described, provided spectral and analytical data as described (Njar et al., *J. Med. Chem.*, 1998, 41, 902-912).

3β-Acetoxy-17-(1H-benzimidazol-1-yl)-16-formylandrosta-5,16-diene (3): A mixture of 3β-Acetoxy-17-chloro-16-formylandrosta-5,16-diene (2, 2.5 g, 6.65 mmol), benzimidazole (2.35 g, 19.9 mmol), and $K_2CO_3$ (2.76 g, 23.9 mmol) in dry DMF (20 mL) is stirred at ca. 80° C. under Ar for 1.5 h. After cooling to room temperature, the reaction mixture is poured onto ice-cold water (250 mL) and the resulting precipitate is filtered, washed with water, and dried to give a crude dirty white solid (ca. 2.9 g). Purification by FCC [petroleum ether/EtOAc/$Et_3N$ (6:4:0.3)] gives 2.7 g (88.7%) of pure compound 3: mp 227-230° C.; IR ($CHCl_3$) 3691, 3024, 2951, 2359, 1725, 1670, 1604, 1491, 1452, 1375, 1253, 1032, 897, 852, 818, 700, 657, 618, 576, 565, 550, 529, 511, 476 $cm^{-1}$; $^1H$ NMR (300 MHz, $CDCl_3$) δ 1.07 (s, 6H, 18- and 19-$CH_3$), 2.04 (s, 3H, 3β-OCH$_3$), 4.60 (m, 1H, 3α-H), 5.43 (br s, 1H, 6-H), 7.35 (br. s, 2H, aromatic-Hs), 7.85 (s, 1H, aromatic-H), 7.98 (s, 1H, aromatic-H), 7.98 (s, 1H-$2^1$-H) and 9.59 (s, 1H, 16-CHO). HRMS calcd 481.2462 ($C_{29}H_{34}O_3N_2.Na^+$). found 481.2454.

3β-Acetoxy-17-(1H-benzimidazol-1-yl)androsta-5,16-diene (4): A solution of 3β-Acetoxy-17-(1H-benzimidazol-1-yl)-16-formylandrosta-5,16-diene (3, 2.04 g, 4.45 mmol) in dry benzonitrile (10 mL) was refluxed in the presence of 10% palladium on activated charcoal (1.02 g, i.e., 50% weight of 3) for 5 h. After cooling to room temperature, the catalyst was removed by filtration through a Celite pad. The filtrate was evaporated, and the residue was purified by FCC [petroleum ether/EtOAc/$Et_3N$ (7.5:3:0.5)] gave 1.41 g (73.8%) of pure compound 4: mp 159-160° C.; IR($CHCl_3$) 3687, 2947, 2854, 2358, 2340, 1725, 1633, 1609, 1557, 1489, 1454, 1373, 1291, 1253, 1195, 1136, 1031, 985, 910, 839, 735, 665, 590, 544, 533, 513, 502, 488 $cm^{-1}$; $^1H$ NMR (300 MHz, $CDCl_3$) δ 1.02 (s, 3H, 18-$CH_3$), 1.07 (s, 3H, 19-$CH_3$), 2.04 (s, 3H, 3β-OCH$_3$), 4.62 (m, 1H, 3α-H), 5.43 (br s, 1H, 6-H), 5.98 (s, 1H, 16-H), 7.30 (m, 2H, aromatic-Hs), 7.49 (s, 1H, aromatic-H), 7.81 (s, 1H, aromatic-H), and 7.95 (s, 1H, $2^1$-H). HRMS calcd 453.2512 ($C_{28}H_{34}O_2N_2.Na^+$). found 453.2511.

3β-Hydroxy-17-(1H-benzimidazol-1-yl)androsta-5,16-diene (5): The acetate 4 (1.3 g 3.02 mmol) was dissolved in methanol (20 mL) under an inert Ar atmosphere, and the resulting solution treated with 10% methanolic KOH (8 mL). The mixture was stirred at room temperature for 1.5 h, and then concentrated under reduced pressure at approx. 40° C. to a volume of 10 mL. This solution was poured into ice water (300 mL), and the resulting white precipitate was filtered, washed with water and dried. Crystallization from EtOAc/MeOH gave 5 (1.10 g, 94%), mp 189-190° C.; IR($CHCl_3$) 2934, 2339, 1609, 1490, 1453, 1291, 1040, 837, 808, 705, 663, 608, 578, 550, 517 $cm^{-1}$; $^1H$ NMR (300 MHz, $CDCl_3$) δ 1.02 (s, 3H, 18-$CH_3$), 1.07 (s, 3H, 19-$CH_3$), 3.55 (m, 1H, 3α-H), 5.41 (br s, 1H, 6-H), 5.99 (s, 1H, 16-H), 7.30 (m, 2H, aromatic-Hs), 7.54 (s, 1H, aromatic-H), 7.80 (s, 1H, aromatic-H), and 7.96 (s, 1H, $2^1$-H). HRMS calcd 411.2407 ($C_{26}H_{32}ON_2.Na^+$). found 411.2396.

17-(1H-benzimidazol-1-yl)androsta-4,16-diene-3-one (6): From a mixture of compound 5 (660 mg, 1.70 mmol), 1-methyl-4-piperidone (2.5 mL), and toluene (40 mL) was distilled off ca. 10 mL. Aluminum isopropoxide (521 mg, 2.55 mmol) was then added, and the mixture was refluxed under Ar for 4 h. After cooling, the mixture was diluted with EtOAc (50 mL), washed successively with 5% aqueous NaHCO$_3$ (x3) and brine (x2), and then dried (Na$_2$SO$_4$). The solvent was evaporated, and the crude product was purified by FCC [$CH_2Cl_2$/EtOH (25:1)] to give the title compound 6 (544 mg, 82%): mp 201-204° C.; IR($CHCl_3$) 2946, 2858, 1622, 1611, 1490, 1453, 1376, 1291, 1270, 1228, 1189, 893, 850, 837, 722, 662, 615, 568, 553, 537, 519 $cm^{-1}$; $^1H$ NMR (300 MHz, $CDCl_3$) δ 1.04 (s, 3H 18-$CH_3$), 1.24 (s, 3H, 19-$CH_3$), 5.78 (s, 1H, 4-H), 5.99 (s, 1H, 16-H), 7.31 (m, 2H, aromatic-Hs), 7.48 (m, 1H, aromatic-H), 7.81 (s, 1H, aromatic-H), and 7.95 (s, 1H, $2^1$-H). HRMS calcd 409.2250 ($C_{26}H_{30}ON_2.Na^+$). found 409.2250.

Reaction of 3β-acetoxy-17-chloro-16-formylandrosta-5,16-diene (2) with benzo-1H-1,2,3-triazole and $K_2CO_3$: 3β-Acetoxy-17-(benzo-2H-1,2,3-triazol-2-yl)-16-formylandrosta-5,16-diene (7a) and 3β-Acetoxy-17-(benzo-1H-1,2,3-triazol-1-yl)-16-formylandrosta-5,16-diene (7b): A mixture of compound 2 (2.5 g, 6.65 mmol), benzotriazole (2.35 g, 19.9 mmol), and $K_2CO_3$ (2.76 g, 23.9 mmol) in dry DMF (20 mL) was stirred at ca. 80° C. under Ar for 45 min. After cooling to room temperature, the reaction mixture was poured onto ice-cold water (250 mL) and the resulting precipitate was filtered, washed with water, and dried to give a crude dirty white solid. Purification by FCC [pet. Ether/EtOAc, (4:1)] first gave 3β-acetoxy-17-(benzo-2H-1,2,3-triazol-2-yl)-16-formylandrosta-5,16-diene (7a, 0.3 g, 9.8%) as minor product; mp 248-250° C.; IR($CHCl_3$) 3023, 2945, 2358, 1725, 1657, 1600, 1375, 1257, 1032, 728, 656, 584, 564, 540, 526, 506, 498 $cm^{-1}$; $^1H$ NMR (300 MHz, $CDCl_3$) δ 1.11 (s, 3H, 18-$CH_3$), 1.37 (s, 3H 19-$CH_3$), 2.04 (s, 3H, 3β-OCH$_3$), 4.62 (m, 1H, 3α-H), 5.43 (br s, 1H, 6-1H), 7.43 (d, 1H, J=2.4 Hz, aromatic-Hs), 7.45 (d, 1H, J=2.7 Hz, aromatic-H), 7.88 (d, 1H, J=2.7 Hz, aromatic-H), 7.90 (d, 1H, J=2.4 Hz, aromatic-H) and 10.66 (s, 1H-16-CHO). HRMS calcd 482.2414 ($C_{28}H_{33}O_3N_3.Na^+$). found 482.2413. Further elution with the same solvent system afforded the major product, 30-acetoxy-17-(benzo-1H-1,2,3-triazol-1-yl)-16-formylandrosta-5,16- diene (7b, 2.3 g, 75.4%); mp: 186-188° C.; IR(CHCl$_3$) 3023, 2948, 1725, 1670, 1604, 1488, 1450, 1374, 1253, 1196, 1032, 846, 824, 720, 658, 619, 548, 527, 504, 497 cm$^{-1}$; $^1$H NMR (300 MHz, CDCl$_3$) δ 1.07 (s, 6H, 18- and 19-CH$_3$), 2.04 (s, 3H, 3β-OCH$_3$), 4.60 (m, 1H, 3α-H), 5.43 (br s, 1H, 6-H), 7.46 (m, 2H, aromatic-Hs), 7.57 (d, 1H, J=6.9 Hz, aromatic-H), 8.15 (d, 1H, J=8.4 Hz), aromatic-H), and 9.59 (s, 1H, 16-CHO). HRMS calcd 482.2414 (C$_{28}$H$_{33}$O$_3$N$_3$.Na$^+$). found 482.2416.

3β-Acetoxy-17-(benzo-1H-1,2,3-triazol-1-yl)androsta-5, 16-diene (8): A mixture of bis(triphenyphosphine)rhodium(I) carbonyl chloride (303 mg, 0.438 mmol) and 1,3-bis-(diphenylphosphino)propane (394 mg, 0.954 mmol) in dry xylene (40 mL) was stirred at 80° C. under Ar for 15 min when fine yellow precipitate formed. Compound 7b (1.71 g, 3.72 mmol) was added, and the mixture was refluxed under Ar for 18 h, and then concentrated under reduced pressure. The crude product was purified by FCC [pet ether/EtOAc/Et$_3$N, (8.9:1: 0.1)] to give 1.2 g (74.7%) of pure compound 8; mp 184-186° C. IR(CHCl$_3$) 3063, 2918, 2389, 2358, 1725, 1458, 1373, 1254, 1069, 1031, 843, 809, 786, 692, 646, 560, 535, 528, 512, 494 cm$^{-1}$; $^1$H NMR (300 MHz, CDCl$_3$) δ 1.10 (s, 3H, 18-CH$_3$), 1.25 (s, 3H, 19-CH$_3$), 2.04 (s, 3H, 3β-OCH$_3$), 4.64 (m, 1H, 3α-H), 5.43 (br s, 1H, 6-H), 6.01 (s, 1H, 16-H), 7.40 (t, 1H, J=7.8 Hz, aromatic-H), 7.51 (t, 1H, J=7.8 Hz, aromatic-H), 7.67 (d, 1H, J=8.1 Hz, aromatic-H), and 8.10 (d, 1H, J=8.1 Hz, aromatic-H). FIRMS calcd 454.2465 (C$_{27}$H$_{33}$O$_2$N$_3$.Na$^+$). found 454.2469.

3β-Hydroxy-17-(benzo-1H-1,2,3-triazol-1-yl)androsta-5, 16-diene (9): The method followed that described for compound 5 but using 3β-acetoxy-17-(benzo-1H-1,2,3-triazol-1-yl)androsta-5,16-diene (8; 700 mg, 1.62 mmol). Recrystallization from EtOAc/MeOH give the title compound 9 (600 mg, 95%); mp 241-244° C.; IR(CHCl$_3$) 3603, 2937, 2859, 1609, 1488, 1451, 1373, 1287, 1243, 1069, 1040, 1007, 953, 845, 805, 715, 665, 618, 570, 553, 517 cm$^{-1}$; $^1$H NMR (300 MHz, CDCl$_3$) δ 1.09 (s, 3H, 18-CH$_3$), 1.24 (s, 3H 19-CH$_3$), 3.55 (m, 1H, 3α-H), 5.41 (br s, 1H, 6-H), 6.06 (s, 1H, 16-H), 7.40 (t, 1H, J=7.8 Hz, aromatic-H), 7.52 (t, 1H, J=7.8 Hz, aromatic-H), 7.67 (d, 1H, J=8.1 Hz, aromatic-H), and 8.10 (d, 1H, J=8.1 Hz, aromatic-H). HRMS calcd 412.2359 (C$_{25}$H$_{31}$ON$_3$.Na$^+$). found 412.2365.

17-(benzo-1H-1,2,3-triazol-1-yl)androsta-4,16-diene-3-one (10): The method followed that described for compound 6 but using β-hydroxy-17-(benzo-1H-1,2,3-triazol-1-yl)androsta-5,16-diene (9; 500 mg, 1.28 mmol). Purification of the crude product by FCC [CH$_2$Cl$_2$/EtOH, (50:1)] afforded the titled compound 10 (420 mg, 84.4%); mp: 280-283° C.; IR (CHCl$_3$) 2944, 1658, 1450, 1070, 8444, 825, 721, 624, 589, 564, 554, 541, 521 cm$^{-1}$; $^1$H NMR (300 MHz, CDCl$_3$) δ 1.26 (s, 3H, 18-CH$_3$), 1.27 (s, 3H, 19-CH$_3$), 5.77 (s, 1H, 4-H), 6.01 (s, 1H, 16-H), 7.40 (t, 1H, J=7.8 Hz, aromatic-H), 7.52 (t, 1H, J=7.8 Hz, aromatic-H), 7.67 (d, 1H, J=7.8 Hz, aromatic-H), and 8.10 (d, 1H, J=8.1 Hz, aromatic-H). HRMS calcd 410.2203 (C$_{25}$H$_{29}$ON$_3$.Na$^+$). found 410.2185.

Dehydroepiandrosterone-17 hydrozone (12): Dehydroepiandrosterone (11, 3.5 g, 12.2 mmol) was dissolved in ethanol (60 mL); and the resulting solution was treated with hydrazine hydrate (2.37 mL, 0.049 mol) followed by a solution of hydrazine sulfate (7.9 mg, 0.061 mmol) in 0.25 mL of water. The mixture was stirred at room temperature for 12 h and then poured into ice water. The resulting precipitate was filtered, washed with water, and dried to give white crystals of the titled compound 12; mp: 242-244° C. (lit. 204-206° C.);[22] $^1$H NMR (300 MHz, CDCl$_3$): δ 0.76 (s, 3H, 18-CH$_3$), 1.05 (s, 3H, 19-CH$_3$), 3.74 (br s, 1H, 3-H) and 5.35 (s, 1H, 6-H).

17-Iodoandrosta-5,16-diene-3β-ol (13): A stirred solution of iodine (12.16 g, 0.0203 mol) in dry of THF (144 mL) and dry of Et$_2$O (72 mL) was cooled in an ice bath to 0° C. and the solution was treated with 1,1,3,3, tetramethylguanidine (6.72 mL, 6.24 g, 0.054 mole). A solution of compound 12 (3.0 g, 9.9 mmol) in THF (81 mL) was added dropwise to the iodine solution over 2 h maintaining the reaction temperature at 0° C. The reaction mixture was then concentrated under vacuum, cooled in an ice-bath, and then dried to under vacuum at room temperature to afford a yellow solid (13, 3.65 g, 92.4%). mp: 169-171° C. (lit. 175-176° C.);[22] IR (CHCl$_3$) 2935, 1371, 1039, 862, 843, 799, 715, 665, 582, and 566 cm$^{-1}$; $^1$H NMR (300 MHz, CDCl$_3$): δ 0.76 (s, 3H, 18-CH$_3$), 1.05 (s, 3H, 19-CH$_3$), 3.50 (br s, 1H, 3α-H), 5.35 (s, 1H, 6-H) and 6.14 (s, 1H, 16-H).

3β-Hydroxy-17-(2-pyrazyl)-androsta-5,16-diene (14): A mixture of 17-iodoandrosta-5,16-diene-3β-ol (13; 0.5 g, 1.257 mmol) in solution with dry dimethylformamide (DMF, 10 mL) along with tetrakis(triphenylphosphate) palladium (Pd(PPh$_3$)$_4$) (71.6 mg, 0.062 mmol) and (2-tributylstannyl) pyrazine (774.6 mg, 2.099 mmol) was heated at 120° C. for 20 h. After cooling, the mixture was diluted with cold water (50 mL), and extracted with EtOAc (30 mL×3). The combined EtOAc extract was washed with brine and water, dried over Na$_2$SO$_4$ and then concentrated to give a brownish solid. This crude product was purified by flash column chromatography [FCC, pet.ether/EtOAc/Et$_3$N (3:2:0.15)] to give 14 (66 mg, 15%); mp: 199-201° C. $^1$H NMR (300 MHz, CDCl$_3$): δ 0.94 (s, 3H, 18-CH$_3$), 1.08 (s, 3H, 19-CH$_3$), 3.52 (br s, 1H, 3α-H), 5.40 (s, 1H, 6-H), 6.77 (s, 1H, 16-H), 8.35 (s, 1H, pyrazine-H), 8.48 (s, 1H, pyrazine-H), 8.70 (s, 1H, pyrazine-H). HRMS calcd 350.2358 (C$_{23}$H$_{30}$ON$_2$). found 350.2354.

3β-Hydroxy-17-(5-pyrimidyl)-androsta-5,16-diene (15): Reaction of 13 (0.645 g, 1.623 mmol) as described above for 14, but using (5-tributylstannyl)pyrimidine (1.0 g, 2.710 mmol) dissolved in 10 mL of dry DMF along with (Pd (PPh$_3$)$_4$) (92.88 mg, 0.0804 mmol) and (5-tributylstannyl) pyrimidine (1.0 g, 2.710 mmol) and following purification by [FCC, pet.ether/EtOAc/Et$_3$N (3:2:0.15)] gave 3β-hydroxy-17-(5-pyrimidyl)-androsta-5,16-diene 15 (44 mg, 10%); mp: 231-233° C. (lit. 240-242° C.);[19] $^1$H NMR (300 MHz, CDCl$_3$): δ 1.05 (s, 3H, 18-CH$_3$), 1.08 (s, 3H, 19-CH$_3$), 3.83 (br s, 1H, 3α-H), 5.39 (s, 1H, 6-H), 7.26 (s, 1H, 16-H), 8.73 (s, 2H, 4$^1$-H and 6$^1$-H) and 9.07 (s, 1H, 2$^1$-H). HRMS calcd 350.2358 (C$_{23}$H$_{30}$ON$_2$). found 350.2348.

In Vitro Assay of CYP17: The in vitro CYP17 inhibitory activities of the compounds are evaluated using our rapid acetic acid releasing assay (AARA), utilizing intact P450c17-expressing *E. coli* as the enzyme source (Grigoryev, above). It involves the use of [21-3H]-17α-hydroxypregnenolone as the substrate and CYP17 activity is measured by the amount of tritiated acetic acid formed during the cleavage of the C-21 side chain of the substrate. This establishes that the method is comparable in terms of accuracy and reliability to the HPLC analysis procedure used by researchers in the field (Grigoryev, above). IC$_{50}$ values are obtained directly from plots relating percentage inhibition versus inhibitor concentration over appropriate ranges. Each compound is tested at a minimum of five different concentrations. The assays are performed in triplicate, and the IC$_{50}$ values reported are the mean of triplicate experiments. The standard deviations were ±5% of the mean values.

Human 5α-Reductase Type 1 and 2 Assay: The inhibitory activities of compounds and finasteride as reference are determined using the DU145 cell line (for human type 1 enzyme) and human prostate homogenate (BPH tissue for type 2 enzyme) according to the procedure described by Hartmann and colleagues (Picard et al., "Synthesis and evaluation of 2'-substituted 4-(4'-carboxy- or 4'-carboxymethylbenzylidene)-N-acylpiperidines: Highly potent and in vivo active steroid 5α-reductase type 2 inhibitors", *J. Med. Chem.,* 2002, 45, 3406-3417). The percent inhibition values at a concentration of 10 μM or, in case of more potent compounds, the $IC_{50}$ values are determined.

Competitive Androgen Receptor (AR) Binding and Luciferase Assays:

AR Binding/Competition Assay: Wells in 24-well multiwell dishes are coated with poly-1-lysine (0.05 mg/ml) for 5 minutes, dried, rinsed with sterilized, distilled, water, and dried for 2 hours. To determine the kinetics of R1881 binding to the LNCaP AR and the wild-type AR, LNCaP and PC3AR cells are plated ($2-3\times10^5$) in 24 well multiwell dishes in steroid-free medium and allowed to attach. The following day the medium is replaced with serum-free, steroid free RPMI supplemented with 0.1% BSA and containing [$^3$H]R1881 (0.01-10 nM) in the presence or absence of a 200 fold excess of cold DHT, to determine nonspecific binding, and 1 μM triamcinolone acetonide to saturate progesterone and glucocorticoid receptors. Following a 2-hour incubation period at 37° C., cells are washed twice with ice-cold DPBS and solubilized in DPBS containing 0.5% SDS and 20% glycerol. Extracts are removed and cell associated radioactivity counted in a scintillation counter. The data is analyzed, including Kd and Bmax determination, by nonlinear regression using Graphpad Prism software. When the concentration required to almost saturate AR in both cell lines is established, the ability of the test compounds (0.1 nM-10 μM) to displace [$^3$H]R1881 (5.0 nM) from the receptors is determined as described above. The $IC_{50}$ of each compound is determined by nonlinear regression with Graphpad Prism software (GraphPad Software, Inc, San Diego, Calif.).

Luciferase Transactivation Assay: Transcriptional activation assay is carried out as described previously by Kim et al., above, with minor modifications. The Probasin luciferase reporter construct ARR2-Luc is generated by insertion of the minimal probasin promoter ARR2, kindly provided by Dr R Matusik of Vanderbilt University Medical Center (*Endocrinology,* 2000, 141: 4698-4710) into the polyclonal linker region of PGL3-enhancer vector (Promega). The pRL-null (Promega) is used as the internal control. Briefly, LNCaP cells grown in 24-well plates coated with poly-L-lysine were transfected with ARR2-Luc in the phenol-red free RPMI 1640 medium containing 5% charcoal-stripped FBS (Hyclone). 24 h post-transfection, the cells are incubated with fresh phenol-red free serum-free RPMI 1640 medium with or without DHT and inhibitors for 18 h. Luciferase activities are measured in triplicates by using dual luciferase assay system according to the manufacturer's instruction (Promega). The results are presented as the fold induction, that is, the relative luciferase activity of the treated cells divided by that of the control.

Cell Culture and Viability Assay: LNCaP cells are grown in RPMI 1640 medium supplemented with 10% FBS and 1% penicillin/streptomycin solution. To determine the effect of novel compounds on cell proliferation, cells are transferred into steroid-free medium three days prior to the start of the experiments. Steroid-free medium consisted of phenol red free RPMI supplemented with 5% dextran-coated, charcoal treated serum, and 1% penicillin/streptomycin solution. Growth studies are then performed by plating cells ($3\times10^4$) in 24-well multi-well dishes (Corning, Inc. Corning, N.Y.). After a 24 hours attachment period, the medium is aspirated and replaced with steroid-free medium containing vehicle or the indicated concentration of DHT (1 nM) and compounds (0.1 μM-10 μM). Control wells are treated with vehicle (ethanol). This medium is changed every three days and the number of viable cells is compared by WST-1 [4-[3-(4-iodophenyl)-2-(4-nitrophenyl)-2H-5-tetrazolio]-1,3-benzene disulfonate] assay on the seventh day. Following incubation of cells for the above-mentioned time, 10% WST-1 solution is added to each well and incubated at 37° C. for three hours. Following incubation, plates are slightly shaken and immediately read at 450 nm with a scanning multi-well spectrophotometer. All results represent the average of a minimum of three wells. Additional control consists of medium alone with no cells.

Pharmacokinetic Studies All animal studies are performed according to the guidelines and approval of the Animal Care Committee of the University of Maryland School of Medicine, Baltimore. Male SCID mice weighing 20-22 gm (8-10 weeks old) obtained from NCI, Frederick, Md., USA are maintained in a controlled environment of about 25° C., 50% relative humidity and 12 h of light and 12 h of dark cycles and allowed free access to food and water. Compounds 5 and 6 are formulated in 40% β-cyclodextrin in water and a single subcutaneous dose is given to mice. The animals are sacrificed at various times up to 6 h after drug administration and blood was obtained by cardiac puncture under light halothane (Ayerst, New York, N.Y., USA) anesthesia.

HPLC Analysis: Chromatographic separations and quantification of the steroids and the appropriate internal standards are achieved by a reverse phase HPLC method on a Waters® Novapak® C18 column (3.9×150 mm) protected by Waters® guard cartridge packed with pellicle C18 as previously described. Briefly, the HPLC system used in this study consisted of Waters® solvent delivery system, Waters® controller (Milford, Mass.), coupled to a Waters® 717$^{plus}$ autosampler and a Waters® 996 photodiode array detector operated at 242.7 nm. The mobile phase composition is Water/MeOH/$CH_3CN$ (35:35:30, v/v/v+200 μl, of $Et_3N$ and 0.77 g of $NH_4OAc$ per 1000 mL of mobile phase) at a flow rate of 1.0 mL/min. The HPLC analysis is performed at ambient temperature and data acquisition and management ius achieved with a Waters® millennium chromatography manager.

Sample Preparation: Test tubes containing mouse plasma (200 μL), 5 or 6 and VN/85-1 (internal standard, 10 μL of 100 μg/mL), are extracted with diethyl ether (2×2 mL) using a vortex mixer for 3 minutes and centrifuged at 3000 g for 5 min. The organic layers are evaporated to dryness under a gentle stream of air. The residue is reconstituted in an aliquot of the mobile phase (100 μL) and filtered using 0.2 μm Teflon filters before HPLC analysis. Calibration Curve and HPLC Assay Validation: The calibration curves for 5 in plasma and tissue and for 6 in plasma are constructed by spiking varying amounts of the compounds into extraction tubes (duplicate) containing plasma (200 μL) and tissue preparations (200 μL) from untreated animals to give final concentrations of 0.1-100.0 μg/mL. Appropriate blank extraction tubes are also prepared and an aliquot of the internal standard is added into each extraction tube to give a final concentration of 5 μg/ml. The calibration samples are taken through the sample preparation procedure as described above. An aliquot of the reconstituted extract (50 μl) is injected into the HPLC system and the ratio of the peak areas for each analyte to that of the internal standard are plotted against concentrations of 5 or 6. The precision and accuracy of the assays are determined from a range of known concentrations of the inhibitors in blank plasma and taken through the HPLC procedure. The study is repeated on three separate occasions.

Data Analysis: Pharmacokinetic calculations are performed as previously described. The non-compartmental pharmacokinetic calculations are performed using WinNOnlin (Scientific Consulting Inc.). One-way analysis of variance (ANOVA) on SigmaStat for Windows version 1.0 is used to compare different treatment groups at the 95% confidence level. The Bonferroni post-hoc test is used for determination of significance. A P-value of less than 0.05 is considered as statistically significant.

In Vivo Antitumor Studies (LAPC-4 Prostate Cancer Xenografts): All animal studies are performed according to the guidelines and approval of the Animal Care Committee of the University of Maryland School of Medicine, Baltimore. Male severe combined immunodeficient (SCID) mice 4-6 weeks of age purchased from the National Cancer Institute-Frederick Cancer Research and Development Center (Fredrick, Md.) are housed in a pathogen-free environment under controlled conditions of light and humidity and allowed free access to food and water. Tumors are developed from LAPC4 cells inoculated subcutaneously (s.c.) in the mice essentially as previously described (21). LAPC4 cells are grown in IMEM with 15% FBS plus 1% PS and 10 nm DHT until 80% confluent. Cells are scraped into DPBS, collected by centrifugation, and resuspended in Matrigel (10 mg/ml) at $3 \times 10^7$ cells/ml. Mice are injected s.c. with 100 µl of the cell suspension at one site on each flank. Tumors are measured weekly with calipers, and tumor volumes are calculated by the formula: $4/3\pi \times r_1^2 \times r_2 < r_2$).

In the first experiment, LAPC4 tumors are allowed to grow for 8-10 weeks following inoculation. Groups of 5 mice with comparable total tumor volumes are either castrated or treated with 5 and 6 (0.15 mmol/kg once-daily and 0.15 mmol/kg twice-daily, 9 a.m. and 5 p.m.). Mice are castrated under methoxyfluorane anesthesia. Compounds 5 and 6 were prepared at 17.2 mg/ml in a 0.3% solution of hydroxypropyl cellulose in saline, and mice receiv s.c. injections daily. Control and castrated mice are treated with vehicle only. Tumors are measured weekly for the 4 weeks of treatment and tumor volumes are calculated. At the end of the treatment period, the animals are sacrificed under halothane anesthesia; tumors are excised, weighed and stored at −80° C. Animals are also weighed weekly and monitored for general health status and signs of possible toxicity due to treatment.

In the second experiment, mice are inoculated with LAPC4 cells and are divided into four groups of 5 mice each. The control and castrated group receiv vehicle, while the other two groups receiv either VN/85-1 (0.15 mmol/kg twice-daily, 9 a.m. and 5 p.m.) or 5 (0.15 mmol/kg twice-daily, 9 a.m. and 5 p.m.). These treatments are initiated one day after LAPC4 cell inoculation; continued for 14 weeks for control group, 19 weeks (for VN/85-1 and castration groups) and for 21 weeks for 5 treated group and tumors are measured and processed as described above.

Measurement of 5 (VN/124-1) levels in tumor, liver and testes: The animals in the VN/124-1-treated group are sacrificed 1 h after the last VN/124-1 administration, and tumor, liver and testis are harvested and snap frozen in liquid nitrogen. Tissue samples are homogenized in phosphate buffer (pH=7.4, 0.5 ml/mg of tissue). Homogenized tissue (200 µl) is spiked with the internal standard, VN/85-1 (104 from 100 µg/mL stock solution), and then extracted with $Et_2O$ (2×2 mL) by vortexing for 3 min followed by centrifugation at 3000 g for 5 min. The $Et_2O$ extract is separated and evaporated to dryness under a gentle stream of air. The residue is reconstituted in 100 µL of the HPLC mobile phase, filtered through 0.2 µm Teflon filters and then analyzed by HPLC as described above.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

TABLE 1

CYP17 and 5α-reductase activities and androgen receptor binding of novel 17-heteroaryl compounds.

| Compound[a] | CYP17 $IC_{50}$ (nM)[b] | 5α-Reductase % inhibition at 10 µM [$IC_{50}$ (nM)][b] | | AR Binding $IC_{50}$ (nM)[c] | |
|---|---|---|---|---|---|
| | | type 1[d] | type 2[e] | LNCaP | PC3-AR |
| 5 | 300.0 | 4 | 53 | 845 | 384 |
| 6 | 915.0 | [770] | [480] | 1200 | 242 |
| 9 | 1250.0 | ni[f] | 17 | — | — |
| 10 | 5817.4 | 21 | 56 | — | — |
| 14 | 3810.0 | — | — | — | 366 |
| 15 | 500.0 | — | — | — | 374 |
| For comparison | | | | | |
| VN/85-1 | 50.0 | — | — | — | — |
| Abiraterone | 800.0 | — | — | — | — |
| Ketoconazole | 1100.0 | — | — | — | — |
| Finasteride | — | [60.0] | [2.0] | — | — |
| Casodex | — | — | — | 940 | — |
| Flutamide | — | — | — | 11600 | 10985 |

[a]We have previously reported the synthesis of VN/85-1 (Njar et al., above) Abiraterone was synthesized as described by Potter et al (A convenient, large-scale synthesis of abiraterone acetate [3β-acetoxy-17(3-pyridyl)androsta-5,16-diene], a potential new drug for the treatment of prostate cancer. Org. Prep. Proc. Int., 1997, 29, 123-128).
[b]$IC_{50}$ is the concentration of inhibitor required to inhibit the enzyme activity by 50%, each in duplicate for CYP17, triplicate for 5α-reductase and AR binding.
[c]$IC_{50}$ is the concentration of compound required for a 50% displacement of [$^3$H]R1881 from the androgen receptor.
[d]Prostatic tumor cell line (DU-145) expressing type 1 enzyme; substrate: 5 nM [1β-$^3$H] androstenedione.
[e]Enzyme from BPH tissue (type 2 enzyme), 125 µg of protein, substrate: 210 nM [1β,2β-$^3$H]testosterone.
[f]ni = no inhibition up to 10 µM.
— = not determined.

TABLE 2

Pharmacokinetic parameters for 5 (50 and 100 mg/kg) and 6 (50 mg/kg) after s.c. administration.

| | Parameter[a] | | |
|---|---|---|---|
| | 5 | | 6 |
| | 50 mg/kg | 100 mg/kg | 50 mg/kg |
| $t_{1/2}$ (min) | 44.17 ± 1.15 | 36.6 ± 1.6 | 37.93 ± 1.15 |
| $K_{el}$ (min$^{-1}$) | 56.5 ± 0.94 | 68.49 ± 1.26 | 0.0183 ± 0.004 |
| AUC (min.µg/mL) | 1440.00 ± 60.23 | 1813.94 ± 10.94 | 647.10 ± 20.23 |

TABLE 2-continued

Pharmacokinetic parameters for 5 (50 and 100 mg/kg) and 6 (50 mg/kg) after s.c. administration.

| | Parameter[a] | | |
|---|---|---|---|
| | 5 | | 6 |
| | 50 mg/kg | 100 mg/kg | 50 mg/kg |
| $T_{max}$ (min) | 30.00 ± 0.0 | 30.00 ± 0.0 | 60.00 ± 0.00 |
| $C_{max}$ (μg/mL) | 16.82 ± 0.37 | 32.23 ± 0.34 | 5.15 ± 0.09 |
| MRT (min) | 65.40 ± 0.60 | 60.46 ± 1.54 | 79.95 ± 0.01 |
| $V_d$ (mL/kg) | 2098.99 ± 4. | 113276.39 ± 26.71 | 4207.24 ± 6.25 |

[a]Values are expressed as mean ± S.E., n = 5.

BRIEF DESCRIPTION OF SCHEMES AND FIGURES

Chart 1: Structures of abirateron and VN/85-1 (16)

Scheme 1: Synthesis of 17-benzoazole compounds (5, 6, 9 and 10).

Scheme 2: Synthesis of 17-diazine compounds (14 and 15).

Scheme 3: Synthesis of metabolites of trans-androsterone, including VNLG/81.

FIG. 1: The effects of 5, 6 and casodex on transcriptional activity of luciferase mediated through LNCaP-AR in LNCaP-ARR2-1u prostate cancer cells. Cells in steroid-free medium were treated with vehicle, or increasing concentrations of either 5 or casodex with and without 1 nM DHT for 18 h. Cells were then assayed for luciferase activity as described in "Materials and Methods". The bars represent the mean light units [counts per second (cps)/unit protein, i.e., relative luciferase activity] in triplicate wells from three separate experiments.

FIG. 2: The effects of 5, 6 and casodex on (a) LNCaP and (b) LAPC4 prostate cancer cell growth. Cells were grown in steroid-free medium before plating. Triplicate wells were then co-treated with increasing concentrations of 5, 6 or casodex and DHT as described in "Materials and Methods." The percentage (compared to control) of growth inhibition after 7 days of treatment was determined using WST-1 assay. The results represent the average and standard deviation of three experiments performed in triplicate.

FIG. 3: Typical HPLC chromatogram of 5, 16 (internal standard) and metabolite extracted from mouse plasma. The retention times for 16, metabolite, and 5 were 11.5, 17.3 and 21.6 min, respectively.

FIG. 4: Pharmacokinetic profiles of 5 and 6 following administration of a single subcutaneous bolus dose to male SCID mice. Each data point represents the mean plasma concentions obtained from three mice. The standard deviations (not shown) were ±5-8% of the mean values.

FIG. 5: Pharmacokinetic profiles of 5 and metabolite following a single subcutaneous bolus dose (100 mg/kg·bw) of 5 to male mice.

FIG. 6: In vivo antitumor activity of 5, 6 and orchidectomy on the growth of LAPC4 prostate tumors in male SCID mice. Groups of five mice with LAPC-4 tumors were treated with 5 (0.15 mmol/kg/day or 0.30 mmol/kg/day). Tumors volumes were measured weekly, and the percentage of change in tumor volume was determined after 28 days of treatment. The standard deviations of tumor volumes (not shown) were ±10-12% of the mean values.

FIG. 7: The effects of 5, 16, and orchidectomy on the formation and growth of LAPC4 prostate tumors in male SCID mice. 3×10[7] LAPC-4 cells were injected s.c. into the dorsal flank of SCID mice. One group of mice was castrated. The other groups of mice received either vehicle or 5 (0.15 mmol/kg twice-daily) or 16 (0.15 mmol/kg twice-daily). Daily treatment with 5 or 16 was initiated 1 day after cell inoculation. Tumors volumes were measured weekly, and the percentage of change in tumor volume was determined after 16 weeks of treatment * Indicates significant difference of 5 versus control, castration and 16 at week 14 (P 0.00065, 0.05 and 0.0097, respectively). ** Indicates significant difference of 5 versus castration and 16 at week 16 (P=0.047 and 0.0047, respectively). ↓-↓↓: Period of reduced administered dose of 5.

Chart 1. Structures of Abiraterone and VN/85-1

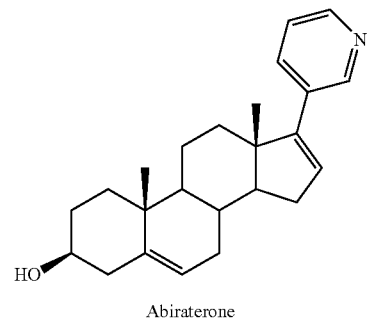

Abiraterone

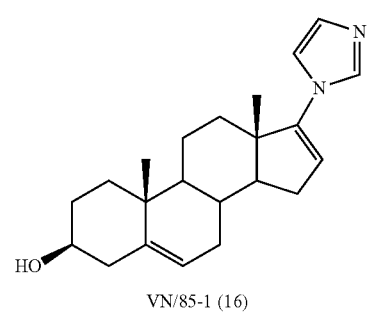

VN/85-1 (16)

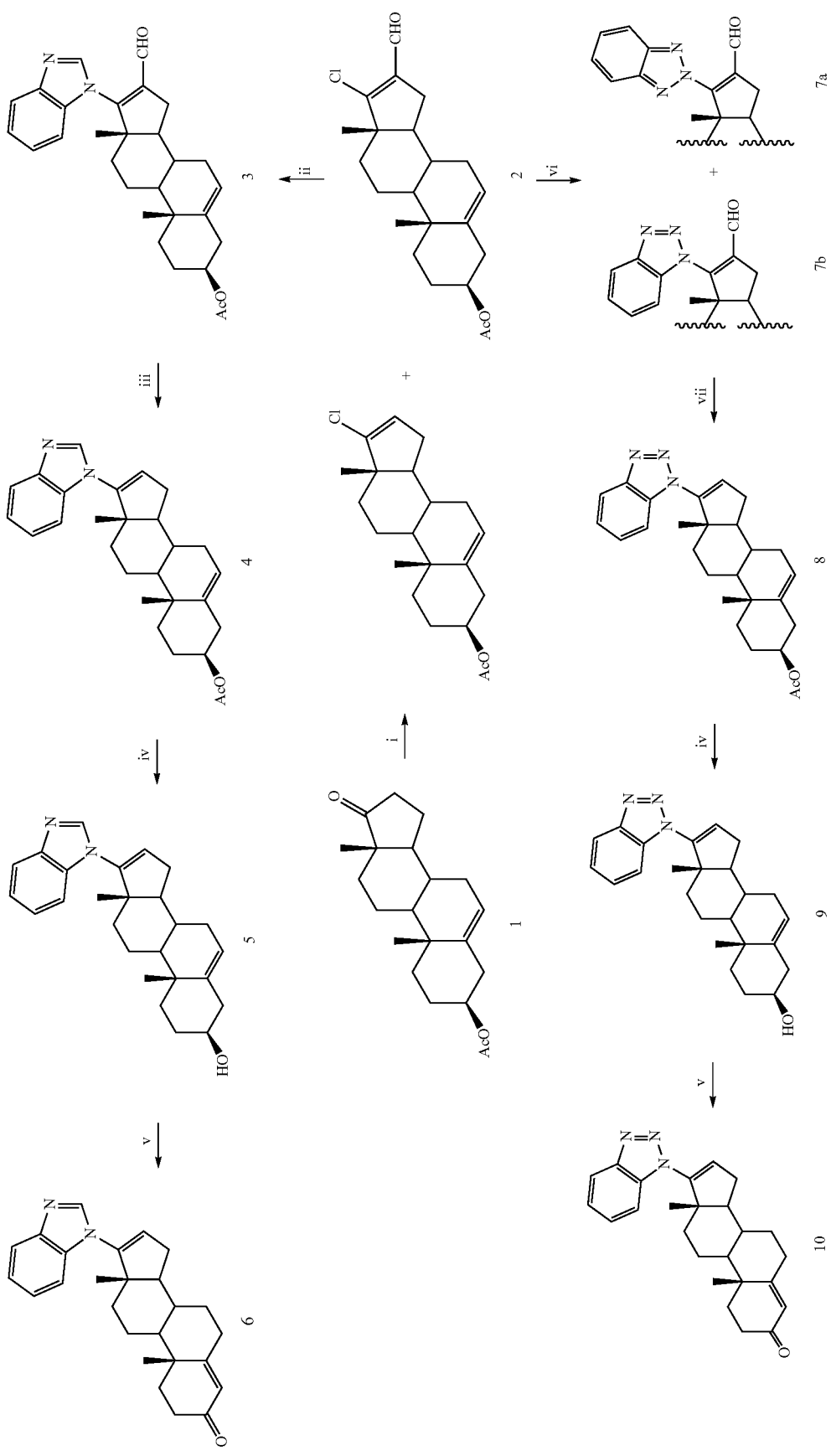
Scheme 1.
(i) POCl₃·DMF, CHCl₃, Ar, reflux; (ii) benzimidazole, K₂CO₃, DMF, Ar, 80° C.; (iii) 10% Pd on activated charcoal, PhCN, reflux; (iv) 10% Methanolic KOH, Ar, rt.; (v) Al(i-PrO)₃, 1-methyl-4-piperidone, toluene, reflux; (vi) benzo-1H-1, 2, 3-triazole, K₂CO₃, DMF, Ar, 80° C.; (vii) (PPh₃)₂RhHCOCl·Ph₂(CH₂)₃PPh₃, xylene, Ar, reflux.

Scheme 2:
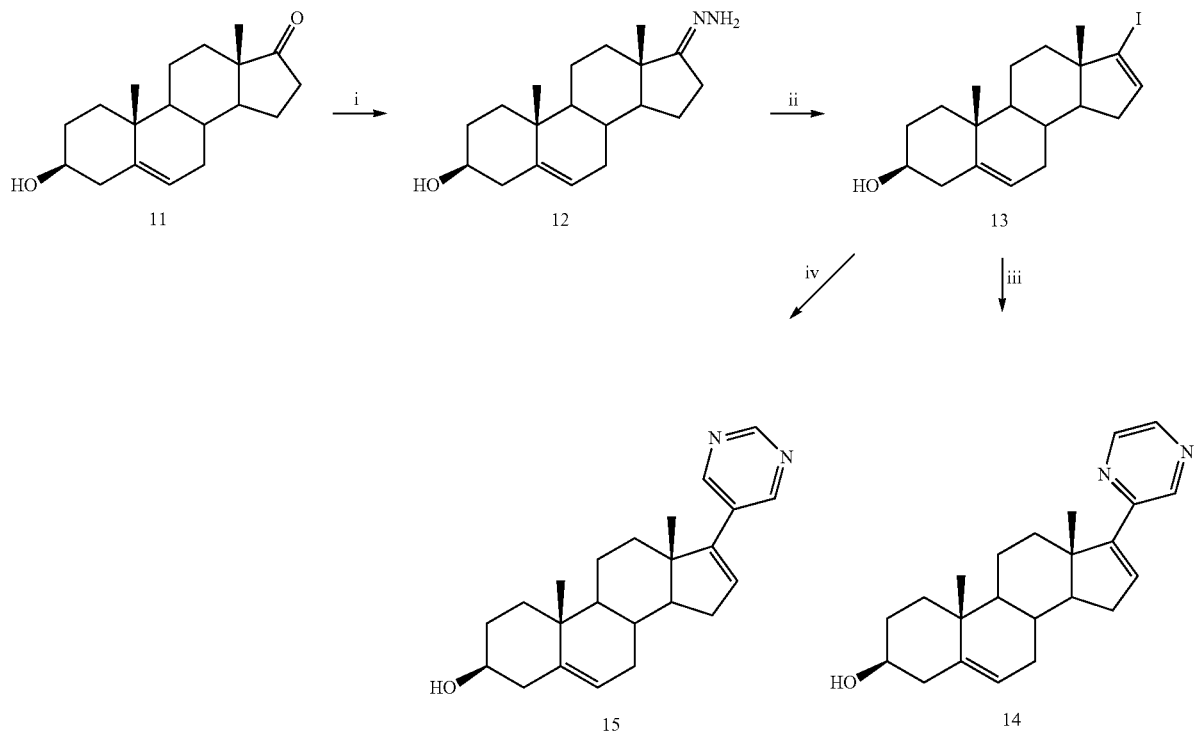
i) $N_2H_4 \cdot H_2O$, $N_2H_4 \cdot H_2SO_4$, EtOH; ii) $I_2$/THF, TG; iii) (2-tributylstannyl pyrazine/Pd(PPh$_3$)$_4$; iv) (5-tributylstannyl)pyrimidine/Pd(PPh$_3$)$_4$

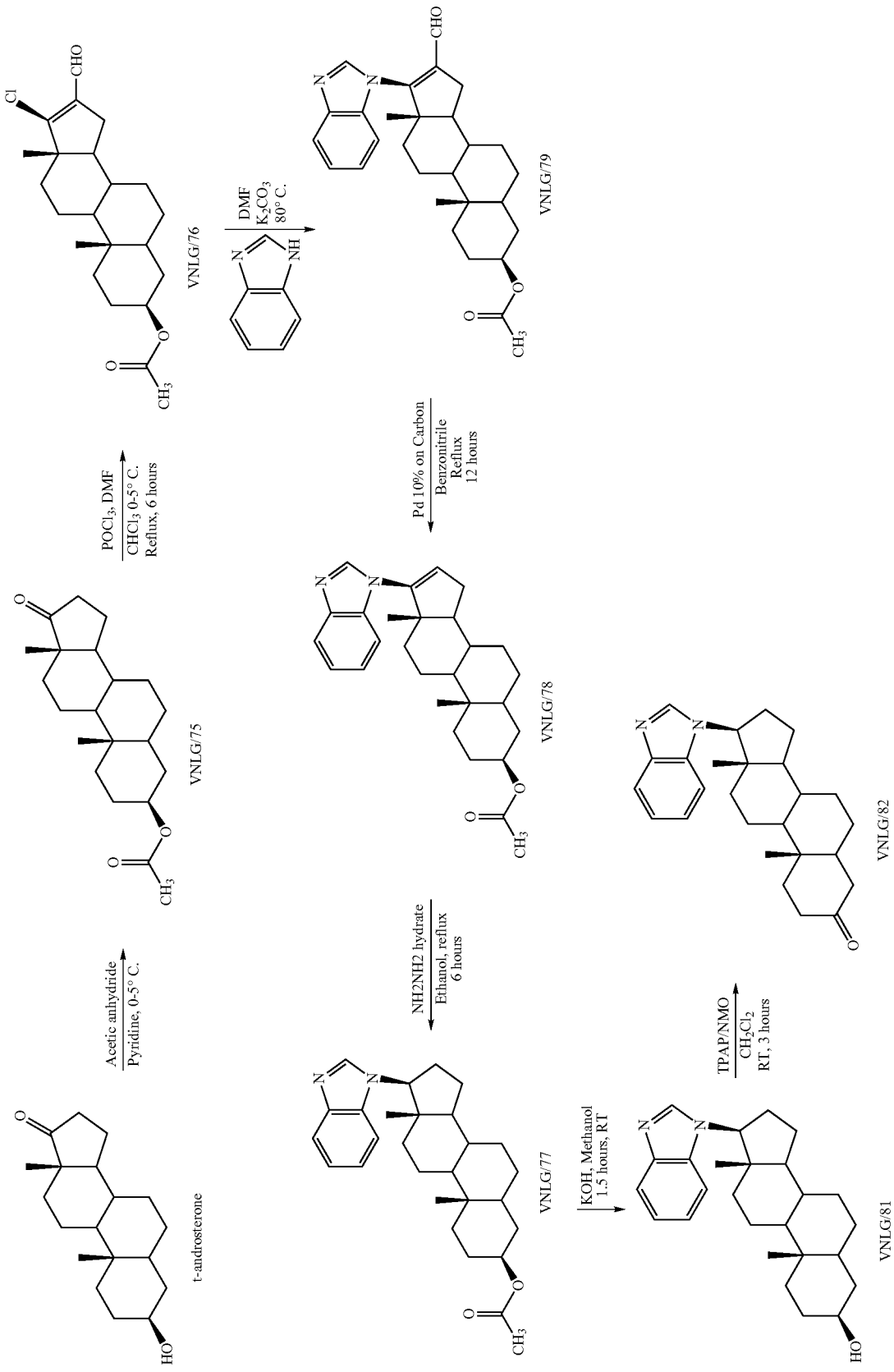
Scheme 3: Synthesis of Metabolites of trans-androsterone, including VNLG/81

We claim:

1. A method of treating prostate cancer in a human subject in need thereof by administering to said subject a compound of the formula:

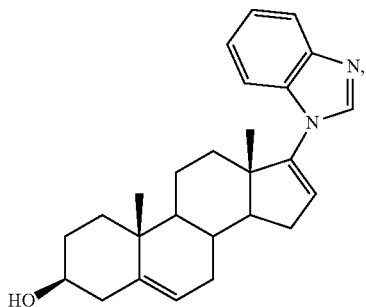

in free base or pharmaceutically acceptable salt form.

2. The method of claim 1, wherein the compound is in a pharmaceutical composition comprising a physiologically acceptable vehicle.

3. The method of claim 1, wherein the compound is in an oral pharmaceutical composition.

4. The method of claim 3, wherein the oral composition is administered to the subject once a day.

5. The method of claim 3, wherein the oral composition is administered to the subject twice a day.

6. The method of claim 3, wherein the oral pharmaceutical composition is in a solid dosage form.

7. The method of claim 6, wherein the solid dosage form is a tablet.

8. The method of claim 6, wherein the solid dosage form is a capsule.

9. The method of claim 1, wherein the compound is in a crystalline form.

10. The method of claim 9, wherein the crystalline form is a free base form.

11. The method of claim 9, wherein the crystalline form has a melting point of about 189-190 degrees Celsius.

12. The method of claim 1, wherein the compound is administered at a dose of more than 0.15 mmol/kg.

13. The method of claim 1, wherein the compound is administered at a dose of less than 0.15 mmol/kg.

14. The method of claim 1, wherein the compound is administered at a dose of between about 0.15 mmol/kg and about 0.30 mmol/kg.

15. The method of claim 1, wherein the compound is administered at a dose of about 1 mg to about 500 mg.

16. The method of claim 1, wherein the compound is administered at a dose of about 50 mg to about 150 mg.

17. The method of claim 1, wherein the compound is administered orally, parenterally, enterally, intraperitoneally, topically, transdermally, ophthalmically, nasally, locally, non-orally, via spray, via inhalation, subcutaneously, intravenously, intramuscularly, buccally, sublingually, rectally, intra-arterially, or intrathecally.

* * * * *